United States Patent
Kirstgen et al.

[11] Patent Number: 6,075,149
[45] Date of Patent: Jun. 13, 2000

[54] 2-PYRAZOLYL OXYPHENYL ACETIC ACID DERIVATIVES, AGENTS CONTAINING THEM AND THEIR USE FOR COMBATING DAMAGING FUNGI AND ANIMAL PESTS

[75] Inventors: Reinhard Kirstgen, Neustadt; Herbert Bayer, Mannheim; Norbert Götz, Worms; Wassilios Grammenos, Ludwigshafen; Thomas Grote, Schifferstadt; Bernd Müller, Frankenthal; Ruth Müller, Friedelsheim; Klaus Oberdorf; Michael Rack, both of Heidelberg; Franz Röhl, Schifferstadt; Hubert Sauter, Mannheim; Eberhard Ammermann, Heppenheim; Volker Harries, Frankenthal; Gisela Lorenz, Hambach; Siegfried Strathmann, Limburgerhof, all of Germany

[73] Assignee: BASF Aktiengesellschaft, Ludwigshafen, Germany

[21] Appl. No.: 09/091,853
[22] PCT Filed: Dec. 16, 1996
[86] PCT No.: PCT/EP96/05633
  § 371 Date: Jun. 25, 1998
  § 102(e) Date: Jun. 25, 1998
[87] PCT Pub. No.: WO97/24332
  PCT Pub. Date: Jul. 10, 1997

[30] Foreign Application Priority Data

Dec. 27, 1995 [DE] Germany ............ 195 48 786

[51] Int. Cl.[7] .............. C07D 231/22; C07D 231/20; C07D 231/12; A01N 43/56
[52] U.S. Cl. ............ 548/366.1; 548/367.1; 514/407
[58] Field of Search ............ 548/366.7, 367.1; 514/407

[56] References Cited

U.S. PATENT DOCUMENTS

| | | | |
|---|---|---|---|
| 5,298,527 | 3/1994 | Grammenos et al. | 514/539 |
| 5,374,644 | 12/1994 | Clough et al. | 514/375 |
| 5,416,068 | 5/1995 | Grammenos et al. | 504/378 |
| 5,523,280 | 6/1996 | Chene et al. | 504/280 |
| 5,776,965 | 7/1998 | Kim et al. | 514/407 |

*Primary Examiner*—Floyd D. Higel
*Attorney, Agent, or Firm*—Keil & Weinkauf

[57] ABSTRACT

Compounds of the formula I

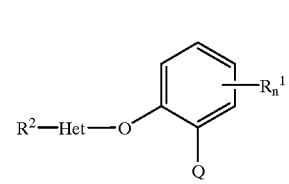

and to salts thereof where the variables having the following meanings:

n is 0, 1, 2, 3 or 4, it being possible for the radicals $R^1$ to be different when n is greater than 1;

Q is $-C(=CHCH_3)-COOCH_3$, $-C(=CHOCH_3)-COOCH_3$, $-C(=NOCH_3)-COOCH_3$ or $-C(=NOCH_3)-NH(CH_3)$;

Het is an unsubstituted or substituted pyrazole ring;

$R^1$ is nitro, cyano, halogen, $C_1-C_4$-alkyl, $C_1-C_4$-haloalkyl, $C_1-C_4$-alkoxy, $C_1-C_4$-haloalkoxy or $C_1-C_4$-alkylthio or unsubstituted or substituted: phenyl, phenoxy or, if n is greater than 1, an unsubstituted or substituted 1,3-butadiene-1,4-diyl group which is bonded to two adjacent carbon atoms of the phenyl radical;

$R^2$ is hydrogen or an unsubstituted or substituted mono- or binuclear carbo- or heterocyclic aromatic ring which is bonded directly or via a group $(-CR^3R^4-)[R^3, R^4=H$ or alkyl or $-CR^3R^4-=(-C(=O)-)$ or $(-C(=NOR^5)-)$; $R^5$=alkyl or alkynyl], compositions comprising them, and the use of the compounds I and of the compositions for controlling harmful fungi and animal pests.

5 Claims, No Drawings

2-PYRAZOLYL OXYPHENYL ACETIC ACID DERIVATIVES, AGENTS CONTAINING THEM AND THEIR USE FOR COMBATING DAMAGING FUNGI AND ANIMAL PESTS

This application is a 371 of PCT/EP 96/05633 filed Dec. 16, 1996.

The present invention relates to compounds of the formula I

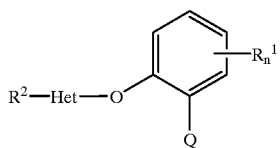

and to salts thereof where the variables having the following meanings:

n is 0, 1, 2, 3 or 4, it being possible for the radicals $R^1$ to be different when n is greater than 1;

Q is —C(=CHCH$_3$)—COOCH$_3$,
  —C(=CHOCH$_3$)—COOCH$_3$,
  —C(=NOCH$_3$)—COOCH$_3$ or
  —C(=NOCH$_3$)CONH(CH$_3$);

Het is a pyrazole ring which has attached to it the radical $R^2$ and which can additionally have attached to it one or, independently of one another, two substituents selected from the group consisting of: chlorine, bromine, methyl and trifluoromethyl;

$R^1$ is nitro, cyano, halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;
  phenyl or phenoxy, each of which can have attached to it one to five halogen atoms and, if desired, together with the halogen atoms, one or, independently of one another, two or three of the following substituents: $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;
  if n is greater than 1, a 1,3-butadiene-1,4-diyl group which is bonded to two adjacent carbon atoms of the phenyl radical and which, in turn, can have attached to it one to four halogen atoms and, if appropriate, together with the halogen atoms, one or, independently of one another, two of the following substituents: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$R^2$ is hydrogen or an unsubstituted or substituted mono- or binuclear aromatic ring which is bonded directly or via a group (—CR$^3$R$^4$—) and which, besides carbon atoms, can contain one to four nitrogen atoms or one or two nitrogen atoms and one oxygen or sulfur atom or one oxygen or sulfur atom as ring members, where $R^3$, $R^4$ independently of one another are: hydrogen or $C_1$–$C_4$-alkyl, or, together with the carbon atom to which they are bonded: a group (—C(=O)—) or (—C(=NOR$^5$)—), where, in turn,
  $R^5$ is $C_1$–$C_4$-alkyl or $C_2$–$C_4$-alkynyl.

The invention furthermore relates to compositions for controlling harmful fungi and animal pests which comprise the compounds I or salts thereof, and to the use of the compounds I and the salts thereof, and of the compositions comprising them, for this purpose.

2-Hetaryloxyphenylacetic acid derivatives which have a fungicidal and, in some cases insecticidal, action have been disclosed in the following publications: EP-A 178 824, EP-A 256 667, EP-A 398 692, EP-A 477 631, EP-A 513 580, WO-A 94/10159 and EP-A 623 604.

The prior-art compounds of this type are as yet unsatisfactory with a view to the ranges of action and application rates.

It is an object of the present invention to remedy this with the aid of the present invention.

We have found that this object is achieved via the compounds I and their salts defined at the outset.

There have furthermore been found compositions for controlling harmful fungi and animal pests which comprise the compounds I or their salts, and the use of the compounds I and their salts and of the compositions comprising them for this purpose.

The compounds I are obtainable by known processes following various routes. In principle, it is irrelevant when synthesizing them whether the group "O-Het-$R^2$" or the group "Q" is constructed first.

The compounds I are obtainable via the compounds Z which, in turn, are accessible by reacting compounds of the formula II with hydroxy heterocycles of the formula III.

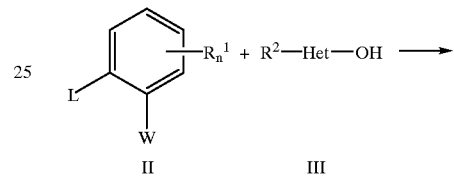

II            III

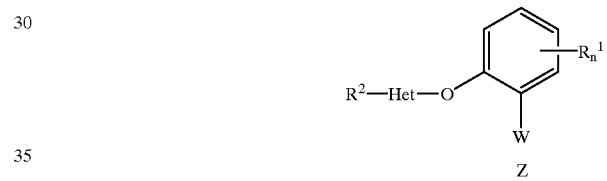

Z

In this formula
L is a leaving group customary for nucleophilic aromatic substitution, such as fluorine, chlorine, bromine or the nitro group;
W is a group which allows or facilitates the nucleophilic exchange of the group L and which can additionally be converted into the group Q of the compounds I—as described below—for example: nitro, —CO—CO—OR', —CO—CO—NHR', —CO—OR' or —CO—CH$_3$ (R'= $C_1$–$C_4$-alkyl).

This reaction is normally carried out at from 0 to 120, preferably from 20 to 60° C.

Suitable solvents are aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone and methyl ethyl ketone, or else dimethyl sulfoxide, dimethylformamide, dimethylacetamide, 1,3-dimethylimidazolidin-2-one and 1,3-dimethyltetrahydro-2 (1H)-pyrimidinone; dimethyl sulfoxide, dimethylacetamide and dimethylformamide are especially preferred.

Mixtures of these may also be used.

The following are generally suitable as bases: basic inorganic compounds, eg. alkali metal hydrides and alkaline earth metal hydrides such as lithium hydride, sodium hydride, potassium hydride, calcium hydride, alkali metal carbonates and alkaline earth metal carbonates such as potassium carbonate and calcium carbonate, furthermore silver carbonate, or else alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride, and alkali metal alkoxides and alkaline earth metal alkoxides such as potassium tert-butoxide and dimethoxymagnesium. Other suitable substances are organic bases, eg. tertiary amines such as trimethylamine, triethylamine, diisopropylethylamine and N-methylpiperidine, pyridine, substituted pyridines such as collidine, lutidine and 4-dimethylaminopyridine, or else bicyclic amines. Especially preferred are sodium hydride, potassium carbonate and potassium tert-butanolate.

In general, the bases are used in equimolar amounts, in an excess or, if appropriate, as solvent.

It may be advantageous for the reaction first to treat the compounds III with base and to react the resulting salt with the compound II.

Furthermore, it may be advantageous for the reaction to add a catalytic amount of a crown ether such as, for example, 18-crown-6 or 15-crown-5, or of another customary phase-transfer catalyst.

Phase-transfer catalysts which can be employed are ammonium halides and ammonium tetrafluoroborates such as benzyltriethylammonium chloride, benzyltributylammonium bromide, tetrabutylammonium chloride, hexadecyltrimethylammonium bromide or tetrabutylammonium tetrafluoroborate, or else phosphonium halides such as tetrabutylphosphonium chloride or tetraphenylphosphonium bromide.

The starting materials II required for the preparation of the compounds I are known from the literature. Those starting materials III which are not already known from the literature can be prepared by processes described therein [1-hydroxypyrazoles: Liebigs. Ann. 1995, page 1563; 3-hydroxypyrazoles: J. Heterocycl. Chem. 30, (1993) page 49; Chem. Ber. 107, (1974) page 1318; Chem. Pharm. Bull. 19, (1971) page 1389; Tetrahedron Lett. 11, (1970) page 875; Chem. Heterocycl. Comp. 5, (1969) page 527; Chem. Ber. 102, (1969) page 3260; Chem. Ber. 109, (1976) page 261; J. Org. Chem. 31, (1966) page 1538; Tetrahedron 43, (1987) page 607; 4-hydroxypyrazoles: CA-A 1 177 081; U.S. Pat. No. 4,621,144; JP-A 60/155,160].

The compounds Z where W is nitro, —CO—OR'; or —CO—CH$_3$ can, in turn, be further reacted in a manner known per se to give the compounds IV.

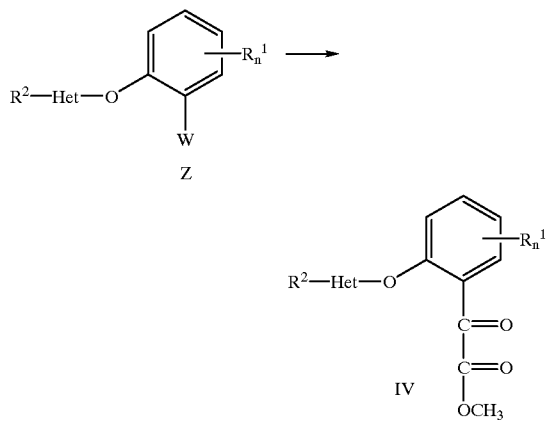

The following overview shows the reactions known per se which are suitable for this conversion:

W=nitro (Cf. EP-A 398 692)
1. Reduction of the nitro group to the amino group (cf. Houben-Weyl, Methoden der Organischen Chemie [Methods in Organic Chemistry], Georg Thieme Verlag, Stuttgart, 4th Edition, Vol. 11/1, page 360 et seq.);
2. Diazotization of the amino group and substitution of the resulting diazonium group by a halogen atom, such as chlorine, bromine or iodine (cf., for example, Houben-Weyl, 4th Edition, Vol. 5/4, page 437 et seq.);
3. Metalation of the aromatic on the position of the halogen atom (cf. EP-A 398 692);
4. Reaction of the metalated aromatic carbon atom with dimethyl oxalate or
5. Instead of 4.: Reaction with oxalyl dichloride and subsequently with methanol (cf. EP-A 398 692).

W=—CO—OR' (cf. EP-A 493 711)
1. Hydrolysis of the —CO—OR' group to the carboxyl group;
2. Reaction of the carboxyl group formed in 1. to the benzoyl cyanide —CO—CN;
3. Pinner reaction on the —CO—CN group;

W=—CO—CH$_3$

Oxidation of the CH$_3$ group (cf.: with potassium permanganate: Houben-Weyl, Vol. 4/1b, page 594 et seq.; with SOCl$_2$: Tetrahedron Lett. 1976, page 2783 et seq.).

The compounds of the formula IV can be further reacted to give the compounds of the formula I.

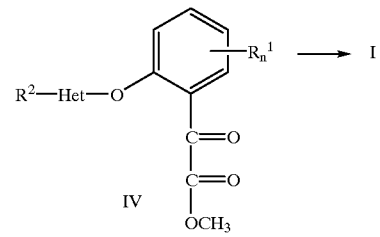

This reaction takes place (cf. WO-A 94/11 334):

in the case of the compounds of the formula I where Q=—C(=CHOCH$_3$)—COOCH$_3$, in a manner known per se, eg. by reacting the compounds of the formula IV with an ylide which is derived from [(C$_6$H$_5$)$_3$P(CH$_2$OCH$_3$)]$^+$Cl$^-$ or from the corresponding bromide;

in the case of the compounds of the formula I where Q=—C(=CHCH$_3$)—COOCH$_3$, in a manner known per se, eg. by reacting the compounds of the formula IV with an ylide which is derived from [(C$_6$H$_5$)$_3$P(CH$_2$CH$_3$)]$^+$Cl$^-$ or from the corresponding bromide;

in the case of the compounds of the formula I where Q=—C(=NOCR$_3$)—COOCH$_3$, in a manner known per se, eg. by reacting the compounds of the formula IV with methylhydroxylamine (CH$_3$ONH$_2$) or its hydrochloride (CH$_3$ONH$_3{}^+$Cl$^-$).

Alternatively, the compounds of the formula I where Q is the group —C(=CHOCH$_3$)—COOCH$_3$ or the group —C(=NOCH$_3$)—COOCH$_3$ can be prepared starting from compounds of the formula Z where W is the group —CO—CH$_3$, when these are first converted into the compounds V by means of rearrangement and oxidation, which are known per se (cf. J. Amer. Chem. Soc. 93 (1971) page 4919; J. Chem. Soc. Perkin Trans. 1 (1977) page 332; Synthesis 1981, page 126):

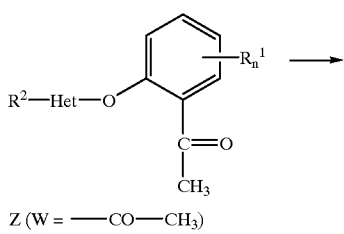

Z (W = —CO—CH$_3$)

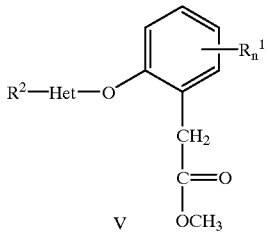

The compounds of the formula V can be further reacted in a manner known per se to give the compounds of the formula I:

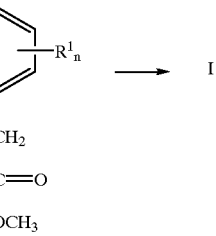

| Compound | Reference |
|---|---|
| I (Q = —C(=CHOCH$_3$)—COOCH$_3$) | EP-A-178 826 |
| | EP-A-256 667 |
| I (Q = —C(=NOCH$_3$)—COOCH$_3$) | EP-A-468 775 |

The compounds of the formula I where Q is a group —C(=NOCH$_3$)—NH(CH$_3$) are obtainable by reacting the corresponding compounds of the formula I where Q=—C(=NOCH$_3$)—COOCH$_3$ with methylamine (cf. Houben-Weyl, 4th Edition, Vol. E5, page 983 et seq.):

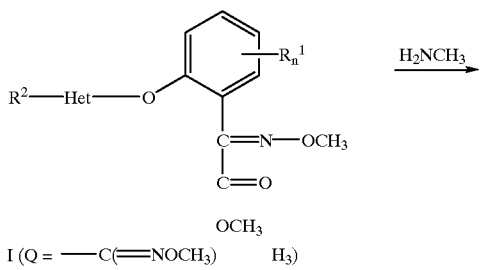

I (Q = —C(=NOCH$_3$)     H$_3$)

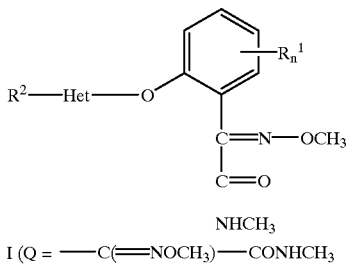

I (Q = —C(=NOCH$_3$)—CONHCH$_3$)

This reaction is normally carried out at from 0 to 60, preferably from 10 to 30° C.

Methylamine can be metered into a solution of I (Q=—C(=NOCH$_3$)—COOCH$_3$) by means of passing in the substance in gaseous form, or as an aqueous solution.

Suitable solvents are aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, alcohols such as methanol, ethanol, n-propanol, isopropanol, n-butanol and tert-butanol, especially preferably methanol, toluene and tetrahydrofuran.

Mixtures of these can also be used.

Upon preparation, the compounds I can be obtained in the form of E/Z isomer mixtures, due to their C=C and C=N double bonds, and these isomer mixtures can be separated into the individual compounds in the customary manner, eg. by crystallization or chromatography.

If isomer mixtures are obtained upon synthesis, a separation of the isomers is, however, not absolutely necessary since some of the individual isomers may be converted into each other during formulation for use, or upon use (eg. when exposed to light, acids or bases). Similar conversions can also take place after application, for example in the case of the treatment of plants, in the treated plant or in the harmful fungus or animal pest to be controlled.

Relative to the C=N or C=C double bond in the group Q, the E isomers of the compounds I (configuration relative to the (OCH$_3$) or the (CH$_3$) group in relation to the COOCH$_3$ or CONHCH$_3$ group are preferred with a view to their activity.

The invention also embraces the salts of the acid-resistant compounds I which contain basic centers, above all basic nitrogen atoms, in particular with mineral acids, such as sulfuric acid and phosphoric acid, or Lewis acids, such as zinc chloride. The type of the salt is normally of no importance. Preferred for the purposes of the invention are those salts which do not damage the plants, areas, materials or spaces to be kept free from harmful fungi or animal pests and which do not adversely effect the activity of the compounds I. Especially important are salts of this type which are suitable for agricultural purposes.

The salts of the compounds I are accessible in a manner known per se, above all by reacting the corresponding compounds I with the abovementioned acids in water or in an inert organic solvent at from −80 to 120, preferably from 0 to 60° C.

Collective terms which generally represent the groups below were used in the definitions of the compounds I given at the outset.

Halogen: fluorine, chlorine, bromine and iodine;

Alkyl: straight-chain or branched alkyl groups having 1 to 4, 6 or 10 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Haloalkyl: straight-chain or branched alkyl groups having 1 to 6 carbon atoms, it being possible for some or all of the hydrogen atoms in these groups to be replaced by halogen atoms as mentioned above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 4 or 6 carbon atoms as mentioned above which are bonded to the skeleton via an oxygen atom (—O—), eg. $C_1$–$C_6$-alkoxy such as methyloxy, ethyloxy, propyloxy, 1-methylethyloxy, butyloxy, 1-methylpropyloxy, 2-methylpropyloxy, 1,1-dimethylethyloxy, pentyloxy, 1-methylbutyloxy, 2-methylbutyloxy, 3-methylbutyloxy, 2,2-dimethylpropyloxy, 1-ethylpropyloxy, hexyloxy, 1,1-dimethylpropyloxy, 1,2-dimethylpropyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy and 1-ethyl-2-methylpropyloxy;

Haloalkoxy: straight-chain or branched alkyl groups having 1 to 6 carbon atoms, it being possible for some or all of the hydrogen atoms in these groups to be replaced by halogen atoms as mentioned above, and these groups being bonded to the skeleton via an oxygen atom;

Alkylthio: straight-chain or branched alkyl groups having 1 to 4 or 6 carbon atoms as mentioned above which are bonded to the skeleton via a sulfur atom (—S—), eg. $C_1$–$C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

The term "partially or fully halogenated" is intended to express that in groups characterized thus some or all of the hydrogen atoms can be replaced by identical or different halogen atoms as mentioned above.

The mono- or binuclear aromatic or heteroaromatic systems mentioned for the radicals can, in turn, be partially or fully halogenated, ie. some or all of the halogen atoms in these groups can be replaced by halogen atoms, such as fluorine, chlorine, bromine and iodine, preferably fluorine and chlorine.

Besides the halogen atoms indicated, these mono- or binuclear aromatic or heteroaromatic systems can additionally have attached to them one to three of the following substituents:

nitro;

cyano, thiocyanato;

alkyl, especially $C_1$–$C_6$-alkyl as mentioned above, preferably methyl, ethyl, 1-methylethyl, 1,1-dimethylethyl, butyl, hexyl, in particular methyl and 1-methylethyl;

alkenyl: straight-chain or branched alkenyl groups having 2 to 6 or 10 carbon atoms and a double bond in any position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl or 1-pentenyl;

alkynyl: straight-chain or branched alkynyl groups having 2 to 10 carbon atoms and a triple bond in any position, eg. $C_2$–$C_4$-alkynyl such as ethynyl, 2-propynyl, 2-butynyl, 3-butynyl or 1-methyl-2-propynyl;

alkylsulfonyl: straight-chain or branched alkyl groups as mentioned above having 1 to 6 or 10 carbon atoms which are bonded to the skeleton via a sulfonyl group (—$SO_2$—);

$C_1$–$C_4$-haloalkyl as mentioned above, preferably trichloromethyl, difluoromethyl, trifluoromethyl, 2,2-difluoroethyl, 2,2,2-trifluoroethyl and pentafluoroethyl;

$C_1$–$C_4$-haloalkylsulfonyl: haloalkyl having 1 to 4 carbon atoms as mentioned above which is bonded to the skeleton via a sulfonyl group (—$SO_2$—);

$C_1$–$C_4$-alkoxy, preferably methoxy, ethoxy, 1-methylethoxy and 1,1-dimethylethoxy, in particular methoxy;

$C_1$–$C_4$-haloalkoxy, in particular $C_1$–$C_2$-haloalkoxy, preferably difluoromethyloxy, trifluoromethyloxy and 2,2,2-trifluoroethyloxy, in particular difluoromethyloxy;

$C_1$–$C_4$-alkylthio, preferably methylthio and 1-methylethylthio, in particular methylthio;

$C_1$–$C_4$-alkylamino such as methylamino, ethylamino, propylamino, 1-methylethylamino, butylamino, 1-methylpropylamino, 2-methylpropylamino and 1,1-dimethylethylamino, preferably methylamino and 1,1-dimethylethylamino, in particular methylamino, di-$C_1$–$C_4$-alkylamino such as N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)-amino, N-butyl-N-(1-methylpropyl)amino, N-butyl-N-(2-methylpropyl)amino, N-butyl-N-(1,1-dimethylethyl)amino, N-(1-methylpropyl)-N-(2- methylpropyl)amino, N-(1,1-dimethylethyl)-N-(1-methylpropyl)amino and N-(1,1-dimethylethyl)-N-(2-methylpropyl)amino, preferably N,N-dimethylamino and N,N-diethylamino, (in particular N,N-dimethylamino;

$C_1$–$C_6$-alkylcarbonyl such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl and 1-ethyl-2-methylpropylcarbonyl, preferably methylcarbonyl, ethylcarbonyl and 1,1-dimethylcarbonyl, in particular ethylcarbonyl;

$C_1$–$C_6$-alkoxycarbonyl such as methoxycarbonyl, ethoxycarbonyl, propyloxycarbonyl, 1-methylethoxycarbonyl, butyloxycarbonyl, 1-methylpropyloxycarbonyl, 2-methylpropyloxycarbonyl, 1,1-dimethylethoxycarbonyl, pentyloxycarbonyl, 1-methylbutyloxycarbonyl, 2-methylbutyloxycarbonyl, 3-methylbutyloxycarbonyl, 2,2-dimethylpropyloxycarbonyl, 1-ethylpropyloxycarbonyl, hexyloxycarbonyl, 1,1-dimethylpropoxycarbonyl, 1,2-dimethylpropyloxycarbonyl, 1-methylpentyloxycarbonyl, 2-methylpentyloxycarbonyl, 3-methylpentyloxycarbonyl, 4-methylpentyloxycarbonyl, 1,1-dimethylbutyloxycarbonyl, 1,2-dimethylbutyloxycarbonyl, 1,3-dimethylbutyloxycarbonyl, 2,2-dimethylbutyloxycarbonyl, 2,3-dimethylbutyloxycarbonyl, 3,3-dimethylbutyloxycarbonyl, 1-ethylbutyloxycarbonyl, 2-ethylbutyloxycarbonyl, 1,1,2-trimethylpropyloxycarbonyl, 1,2,2-trimethylpropyloxycarbonyl, 1-ethyl-1-methylpropyloxycarbonyl and 1-ethyl-2-methylpropyloxycarbonyl, preferably methoxycarbonyl, ethoxycarbonyl and 1,1-dimethylethoxycarbonyl, in particular ethoxycarbonyl;

$C_1$–$C_6$-alkylaminocarbonyl such as methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl, 1,1-dimethylethylaminocarbonyl, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl and 1-ethyl-2-methylpropylaminocarbonyl, preferably methylaminocarbonyl and ethylaminocarbonyl, in particular methylaminocarbonyl;

di-$C_1$–$C_6$-alkylaminocarbonyl, especially di-$C_1$–$C_4$-alkylaminocarbonyl such as N,N-dimethylaminocarbonyl, N,N-diethylaminocarbonyl, N,N-dipropylaminocarbonyl, N,N-di(1-methylethyl)aminocarbonyl, N,N-dibutylaminocarbonyl, N,N-di(1-methylpropyl)aminocarbonyl, N,N-di(2-methylpropyl)aminocarbonyl, N,N-di(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-Dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methyl-propyl)aminocarbonyl, N-(1,1-dimethylethyl)-N-(1-methylpropyl)aminocarbonyl and N-(1,1-dimethylethyl)-N-(2-methylpropyl)aminocarbonyl, preferably N,N-dimethylaminocarbonyl and N,N-diethylaminocarbonyl, in particular N,N-dimethylaminocarbonyl;

$C_1$–$C_6$-alkylcarboxyl such as methylcarboxyl, ethylcarboxyl, propylcarboxyl, 1-methylethylcarboxyl, butylcarboxyl, 1-methylpropylcarboxyl, 2-methylpropylcarboxyl, 1,1-dimethylethylcarboxyl, pentylcarboxyl, 1-methylbutylcarboxyl, 2-methylbutylcarboxyl, 3-methylbutylcarboxyl, 1,1-dimethylpropylcarboxyl, 1,2-dimethylpropylcarboxyl, 2,2-dimethylpropylcarboxyl, 1-ethylpropylcarboxyl, hexylcarboxyl, 1-methylpentylcarboxyl, 2-methylpentylcarboxyl, 3-methylpentylcarboxyl, 4-methylpentylcarboxyl, 1,1-dimethylbutylcarboxyl, 1,2-dimethylbutylcarboxyl, 1,3-dimethylbutylcarboxyl, 2,2-dimethylbutylcarboxyl, 2,3-dimethylbutylcarboxyl, 3,3-dimethylbutylcarboxyl, 1-ethylbutylcarboxyl, 2-ethylbutylcarboxyl, 1,1,2-trimethylpropylcarboxyl, 1,2,2-trimethylpropylcarboxyl, 1-ethyl-1-methylpropylcarboxyl and 1-ethyl-2-methylpropylcarboxyl, preferably methylcarboxyl, ethylcarboxyl and 1,1-dimethylethylcarbonyl, in particular methylcarboxyl and 1,1-dimethylethylcarboxyl;

$C_1$–$C_6$-alkylcarbonylamino such as methylcarbonylamino, ethylcarbonylamino, propylcarbonylamino, 1-methylethylcarbonylamino, butylcarbonylamino, 1-methylpropylcarbonylamino, 2-methylpropylcarbonylamino, 1,1-dimethylethylcarbonylamino, pentylcarbonylamino, 1-methylbutylcarbonylamino, 2-methylbutylcarbonylamino, 3-methylbutylcarbonylamino, 2,2-dimethylpropylcarbonylamino, 1-ethylpropylcarbonylamino, hexylcarbonylamino, 1,1-dimethylpropylcarbonylamino, 1,2-dimethylpropylcarbonylamino, 1-methylpentylcarbonylamino, 2-methylpentylcarbonylamino, 3-methylpentylcarbonylamino, 4-methylpentylcarbonylamino, 1,1-dimethylbutylcarbonylamino, 1,2-dimethylbutylcarbonylamino, 1,3-dimethylbutylcarbonylamino, 2,2-dimethylbutylcarbonylamino, 2,3-dimethylbutylcarbonylamino, 3,3-dimethylbutylcarbonylamino, 1-ethylbutylcarbonylamino, 2-ethylbutylcarbonylamino, 1,1,2-trimethylpropylcarbonylamino, 1,2,2-trimethylpropylcarbonylamino, 1-ethyl-1-methylpropylcarbonylamino and 1-ethyl-2-methylpropylcarbonylamino, preferably methylcarbonylamino and ethylcarbonylamino, in particular ethylcarbonylamino;

$C_3$–$C_7$-cycloalkyl such as cyclopropyl, cyclobutyl, cyclopentyl, cyclohexyl and cycloheptyl, preferably cyclopropyl, cyclopentyl and cyclohexyl, in particular cyclopropyl;

$C_3$–$C_7$-cycloalkoxy such as cyclopropyloxy, cyclobutyloxy, cyclopentyloxy, cyclohexyloxy and cycloheptyloxy, preferably cyclopentyloxy and cyclohexyloxy, in particular cyclohexyloxy;

$C_3$–$C_7$-cycloalkylthio such as cyclopropylthio, cyclobutylthio, cyclopentylthio, cyclohexylthio and cycloheptylthio, preferably cyclohexylthio;

$C_3$–$C_7$-cycloalkylamino such as cyclopropylamino, cyclobutylamino, cyclopentylamino, cyclohexylamino and cycloheptylamino, preferably cyclopropylamino and cyclohexylamino, in particular cyclopropylamino;

heterocyclyl, or heterocyclyloxy, heterocyclylthio and heterocyclylamino: three- to six-membered saturated or partially unsaturated mono- or polycyclic heterocycles which contain one to three hetero atoms selected from a group consisting of oxygen, nitrogen and sulfur and which are bonded to the skeleton directly, or (heterocyclyloxy) via an oxygen atom or (heterocyclylthio) via a sulfur atom or (heterocyclylamino) via a nitrogen atom, eg. 2-tetrahydrofuranyl, oxiranyl, 3-tetrahydrofuranyl, 2-tetrahydrothienyl, 3-tetrahydrothienyl, 2-pyrrolidinyl, 3-pyrrolidinyl, 3-isoxazoldinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydrofur-4-yl, 2,3-dihydrofur-5-yl, 2,5-dihydrofur-2-yl, 2,5-dihydrofur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisothiazol-3-yl, 2,5-dihydroisothiazol-4-yl, 2,5-dihydroisothiazol-5-yl, 2,3-dihydroisopyrazol-3-yl, 2,3-dihydroisopyrazol-4-yl, 2,3-dihydroisopyrazol-5-yl, 4,5-dihydroisopyrazol-3-yl, 4,5-dihydroisopyrazol-4-yl, 4,5-dihydroisopyrazol-5-yl, 2,5-dihydroisopyrazol-3-yl, 2,5-dihydroisopyrazol-4-yl, 2,5-dihydroisopyrazol-5-yl, 2,3-dihydrooxazol-3-yl, 2,3-dihydrooxazol-4-yl, 2,3-dihydrooxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5-dihydrooxazol-5-yl, 2,3-dihydrothiazol-2-yl, 2,3-dihydrothiazol-4-yl, 2y3-dihydrothiazol-5-yl, 4,5-dihydrothiazol-2-yl, 4,5-dihydrothiazol-4-yl, 4,5-dihydrothiazol-5-yl, 2,5-dihydrothiazol-2-y, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol- 5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazeinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, 1,3-dithian-2-yl, Two adjacent radicals on $R^2$ can have the meaning of an unsubstituted or fluorine- and/or chlorine-substituted oxy-$C_1$–$C_2$-alkylideneoxy chain, eg. —O—$CH_2$—O—, —O—$CF_2$—O—, —O—$CCl_2$—O—, —O—$CH_2CH_2$—O—, —O—$CCl_2CCl_2$—O— or —O—$CF_2CF_2$—O—, or of a $C_3$–$C_4$-alkylidene chain, eg. propylidene or butylidene.

Preferred with a view to their activity in the control of harmful fungi and animal pests are those compounds I and their salts where the variables have the following meanings:

n is 0 or 1;

Het is a pyrazole ring which has attached to it the radical $R^2$ and which can additionally have attached to it one or two substituents selected from the group consisting of: chlorine, bromine, methyl and trifluoromethyl;

$R^1$ is halogen, $C_1$–$C_4$-alkyl, $C_1$–$C_2$-haloalkyl, $C_1$–$C_2$-alkoxy, $C_1$–$C_2$-haloalkoxy or $C_1$–$C_2$-alkylthio;

$R^2$ is an unsubstituted or substituted mono- or binuclear carbocyclic a romatic ring where the group (—$CR^3R^4$—) is prefer ably (—CH($CH_3$)—) or (—C(=NOC$H_3$)—), mainly (—$CH_2$—) and in particular a direct bond.

Especially preferred are those compounds I and their salts where the variables have the following meanings:

n is 0 or 1;

Q is —C(=CHOC$H_3$)—COOC$H_3$;

Het is a pyrazole ring which has attached to it the radical $R^2$ and can additionally have attached to it one or two substituents selected from the group consisting of: chlorine, bromine, methyl and trifluoromethyl;

$R^1$ is halogen, $C_1$-$C_4$-alkyl, $C_1$-$C_2$-haloalkyl, $C_1$-$C_2$-alkoxy, $C_1$-$C_2$-haloalkoxy or $C_1$-$C_2$-alkylthio;

$R^2$ is an unsubstituted or substituted mono- or binuclear carbocyclic aromatic ring where the group (—$CR^3R^4$—) is preferably (—$CH(CH_3)$—) or (—$C(=NOCH_3)$—), mainly (—$CH_2$—) and in particular a direct bond.

Furthermore especially preferred compounds I and their salts are those where the variables have the following meanings:

is 0 or 1;

is —$C(=NOCH_3)$—$NH(CH_3)$;

Het is a pyrazole ring which has attached to it the radical $R^2$ and can additionally have attached to it one or two substituents selected from the group consisting of: chlorine, bromine, methyl and trifluoromethyl;

$R^1$ is halogen, $C_1$-$C_4$-alkyl, $C_1$-$C_2$-haloalkyl, $C_1$-$C_2$-alkoxy, $C_1$-$C_2$-haloalkoxy or $C_1$-$C_2$-alkylthio;

$R^2$ is an unsubstituted or substituted mono- or binuclear carbocyclic aromatic ring where the group (—$CR^3R^4$—) is preferably (—$CH(CH_3)$—) or (—$C(=NOCH_3)$—), mainly (—$CH_2$—) and in particular a direct bond.

Also preferred are those compounds of the formula I and their salts where Het has one of the following meanings, the free bond on the left side of the ring in each case having attached to it the radical $R^2$:

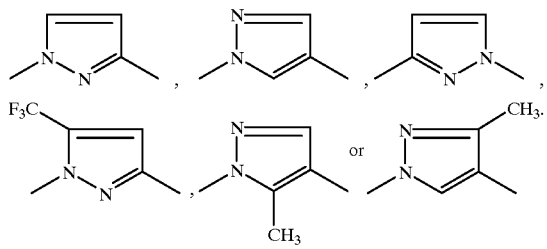

Furthermore preferred are those compounds I where n is 0 or 1.

Equally preferred are those compounds I where $R^1$ is halogen, $C_1$-$C_4$-alkyl, $C_1$-$C_2$-haloalkyl and $C_1$-$C_2$-alkoxy.

Moreover, preferred are those compounds I where $R^2$ is an unsubstituted or substituted mono- or binuclear aromatic radical which, besides carbon atoms, can contain one to four nitrogen atoms or one or two nitrogen atoms and one oxygen or sulfur atom or one oxygen or sulfur atom as ring members.

Particularly preferred are those compounds I where $R^1$ is hydrogen (n=0), chlorine, methyl or trifluoromethyl.

In addition, particularly preferred are those compounds I where $R^2$ is unsubstituted or substituted phenyl which is bonded via a (—$CH_2$—) group and, above all, directly to the radical Het.

Other particularly preferred compounds I are those where $R^2$ is unsubstituted or substituted pyridyl or pyrimidyl and which are bonded to the radical Het via a (—$CH_2$—) group and, above all, directly.

Other particularly preferred compounds I are those where $R^2$ is unsubstituted or substituted phenyl or benzyl. In these cases, preferred substituents of the phenyl radical and of the phenyl ring in the benzyl radical are halogen, cyano, $C_1$-$C_4$-alkyl, $C_1$-$C_4$-alkoxy, $C_1$-$C_2$-haloalkyl, $C_1$-$C_2$-haloalkoxy, $C_1$-$C_4$-alkoxycarbonyl, phenyl and oxy-$C_1$-$C_2$-alkylideneoxy.

Equally preferred are compounds I where $R^2$ is an unsubstituted or substituted six-membered heteroaromatic ring such as pyridyl and pyrimidyl. Preferred substituents of the six-membered heteroaromatic ring are cyano, halogen, $C_1$-$C_4$-alkyl, $C_1$-$C_2$-haloalkyl, $C_1$-$C_4$-alkoxy, $C_1$-$C_2$-haloalkoxy and phenyl.

Very especially preferred with a view to their biological activity are the compounds compiled in the tables below, the double bonds which are adjacent to the phenyl ring having attached to it the group $R_n^1$ in the various groups Q always having the E configuration.

TABLE 1

Compounds of the formula where the radicals $R^1$ and $R^2$ have the meanings which correspond in each case to one line of Table A.

TABLE 2

Compounds of the formula where the radicals $R_n^1$ and $R^2$ have the meanings which correspond in each case to one line of Table A.

TABLE 3

Compounds of the formula where the radicals $R_n^1$ and $R^2$ have the meanings which correspond in each case to one line of Table A.

TABLE 4

Compounds of the formula

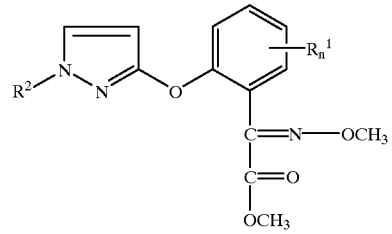

where the radicals $R_n^1$ and $R^2$ have the meanings which correspond in each case to one line of Table A.

TABLE 5

Compounds of the formula

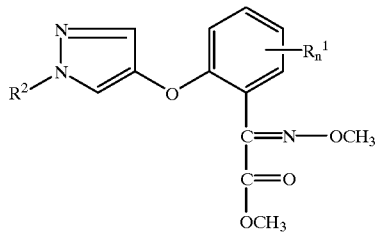

where the radicals $R^1$ and $R^2$ have the meanings which correspond in each case to one line of Table A.

TABLE 6

Compounds of the formula

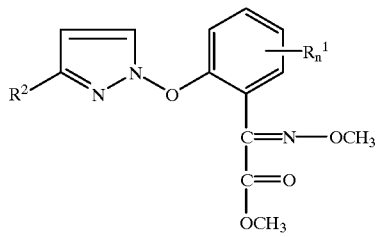

where the radicals $R_n^1$ and $R^2$ have the meanings which correspond in each case to one line of Table A.

TABLE 7

Compounds of the formula

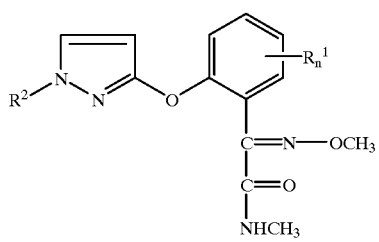

where the radicals $R_n^1$ and $R^2$ have the meanings which correspond in each case to one line of Table A.

TABLE 8

Compounds of the formula

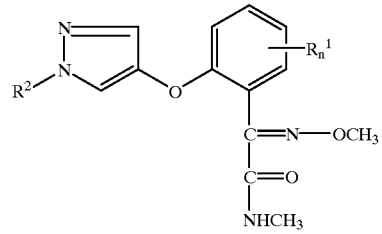

where the radicals $R_n^1$ and $R^2$ have the meanings which correspond in each case to one line of Table A.

TABLE 9

Compounds of the formula

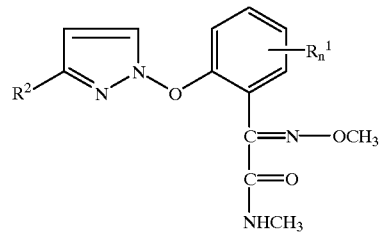

where the radicals $R_n^1$ and $R^2$ have the meanings which correspond in each case to one line of Table A.

TABLE 10

Compounds of the formula

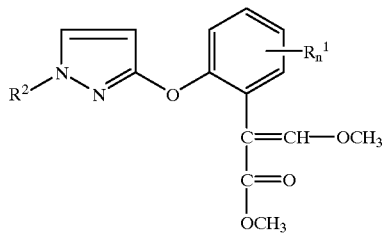

where the radicals $R_n^1$ and $R^2$ have the meanings which correspond in each case to one line of Table A.

TABLE 11

Compounds of the formula

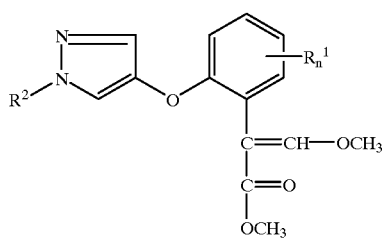

where the radicals $R_n^1$ and $R^2$ have the meanings which correspond in each case to one line of Table A.

TABLE 12

Compounds of the formula $$R^2 \text{-pyrazole-N-O-C}_6H_4(R_n^1)\text{-C(=CH-OCH}_3\text{)-C(=O)-OCH}_3$$

where the radicals $R_n^1$ and $R^2$ have the meanings which correspond in each case to one line of Table A.

TABLE A

| No. | $R_n^1$ | $R^2$ |
|---|---|---|
| A.1 | H | $C_6H_5$ |
| A.2 | 3-Cl | $C_6H_5$ |
| A.3 | 4-Cl | $C_6H_5$ |
| A.4 | 6-Cl | $C_6H_5$ |
| A.5 | 4-F | $C_6H_5$ |
| A.6 | 4-OCH$_3$ | $C_6H_5$ |
| A.7 | 3-CH$_3$ | $C_6H_5$ |
| A.8 | 6-CH$_3$ | $C_6H_5$ |
| A.9 | H | 2-F—$C_6H_4$ |
| A.10 | H | 3-F—$C_6H_4$ |
| A.11 | H | 4-F—$C_6H_4$ |
| A.12 | H | 2,3-F$_2$—$C_6H_3$ |
| A.13 | H | 2,4-F$_2$—$C_6H_3$ |
| A.14 | H | 2,5-F$_2$—$C_6H_3$ |
| A.15 | H | 2,6-F$_2$—$C_6H_3$ |
| A.16 | H | 3,4-F$_2$—$C_6H_3$ |
| A.17 | H | 3,5-F$_2$—$C_6H_3$ |
| A.18 | H | 2-Cl—$C_6H_4$ |
| A.19 | H | 3-Cl—$C_6H_4$ |
| A.20 | H | 4-Cl—$C_6H_4$ |
| A.21 | 3-Cl | 4-Cl—$C_6H_4$ |
| A.22 | 4-Cl | 4-Cl—$C_6H_4$ |
| A.23 | 6-Cl | 4-Cl—$C_6H_4$ |
| A.24 | 4-F | 4-Cl—$C_6H_4$ |
| A.25 | 4-OCH$_3$ | 4-Cl—$C_6H_4$ |
| A.26 | 3-CH$_3$ | 4-Cl—$C_6H_4$ |
| A.27 | 6-CH$_3$ | 4-Cl—$C_6H_4$ |
| A.28 | H | 2,3-Cl$_2$—$C_6H_3$ |
| A.29 | H | 2,4-Cl$_2$—$C_6H_3$ |
| A.30 | H | 2,5-Cl$_2$—$C_6H_3$ |
| A.31 | H | 2,6-Cl$_2$—$C_6H_3$ |
| A.32 | H | 3,4-Cl$_2$—$C_6H_3$ |
| A.33 | H | 3,5-Cl$_2$—$C_6H_3$ |
| A.34 | H | 2,3,4-Cl$_3$—$C_6H_2$ |
| A.35 | H | 2,3,5-Cl$_3$—$C_6H_2$ |
| A.36 | H | 2,3,6-Cl$_3$—$C_6H_2$ |
| A.37 | H | 2,4,5-Cl$_3$—$C_6H_2$ |
| A.38 | H | 2,4,6-Cl$_3$—$C_6H_2$ |
| A.39 | H | 3,4,5-Cl$_3$—$C_6H_2$ |
| A.40 | H | 2-Br—$C_6H_4$ |
| A.41 | H | 3-Br—$C_6H_4$ |
| A.42 | H | 4-Br—$C_6H_4$ |
| A.43 | H | 2,4-Br$_2$—$C_6H_3$ |
| A.44 | H | 2-Br, 4-F—$C_6H_3$ |
| A.45 | H | 2-Br, 4-Cl—$C_6H_3$ |
| A.46 | H | 2-F, 4-Cl—$C_6H_3$ |
| A.47 | H | 3-F, 4-Cl—$C_6H_3$ |
| A.48 | H | 3-Cl, 5-F—$C_6H_3$ |
| A.49 | H | 2-Cl, 4-F—$C_6H_3$ |
| A.50 | H | 2-CN—$C_6H_4$ |
| A.51 | H | 3-CN—$C_6H_4$ |
| A.52 | H | 4-CN—$C_6H_4$ |
| A.53 | H | 3-CN, 4-Cl—$C_6H_3$ |
| A.54 | H | 4-NO$_2$—$C_6H_4$ |
| A.55 | H | 2-CH$_3$—$C_6H_4$ |
| A.56 | H | 3-CH$_3$—$C_6H_4$ |
| A.57 | H | 4-CH$_3$—$C_6H_4$ |
| A.58 | H | 2,4-(CH$_3$)$_2$—$C_6H_3$ |
| A.59 | H | 2,5-(CH$_3$)$_2$—$C_6H_3$ |
| A.60 | H | 2,5-(CH$_3$)$_2$—$C_6H_3$ |
| A.61 | H | 2,6-(CH$_3$)$_2$—$C_6H_3$ |
| A.62 | H | 3,4-(CH$_3$)$_2$—$C_6H_3$ |
| A.63 | H | 3,5-(CH$_3$)$_2$—$C_6H_3$ |
| A.64 | H | 2,4,6-(CH$_3$)$_3$—$C_6H_2$ |
| A.65 | H | 3,4,5-(CH$_3$)$_3$—$C_6H_2$ |
| A.66 | H | 2-CH$_3$, 4-Cl—$C_6H_3$ |
| A.67 | H | 2-Cl, 4-CH$_3$—$C_6H_3$ |
| A.68 | H | 3-CH$_3$, 4-Cl—$C_6H_3$ |
| A.69 | H | 3-Cl, 5-CH$_3$—$C_6H_3$ |
| A.70 | H | 2-CN, 4-CH$_3$—$C_6H_3$ |
| A.71 | H | 2-CH$_3$, 4-CN—$C_6H_3$ |
| A.72 | H | 4-(C$_2$H$_5$)—$C_6H_4$ |
| A.73 | H | 4-[C(CH$_3$)$_3$]—$C_6H_4$ |
| A.74 | H | 3-(C$_6$H$_5$)—$C_6H_4$ |
| A.75 | H | 4-(C$_6$H$_5$)—$C_6H_4$ |
| A.76 | H | 2-CF$_3$—$C_6H_4$ |
| A.77 | H | 3-CF$_3$—$C_6H_4$ |
| A.78 | H | 4-CF$_3$—$C_6H_4$ |
| A.79 | H | 3,5-(CF$_3$)$_2$—$C_6H_3$ |
| A.80 | H | 2-Cl, 4-CF$_3$—$C_6H_3$ |
| A.81 | H | 2-OCH$_3$—$C_6H_4$ |
| A.82 | H | 3-OCH$_3$—$C_6H_4$ |
| A.83 | H | 4-OCH$_3$—$C_6H_4$ |
| A.84 | H | 2,4-(OCH$_3$)$_2$—$C_6H_3$ |
| A.85 | H | 3,4-(OCH$_3$)$_2$—$C_6H_3$ |
| A.86 | H | 2,5-(OCH$_3$)$_2$—$C_6H_3$ |
| A.87 | H | 3,5-(OCH$_3$)$_2$—$C_6H_3$ |
| A.88 | H | 3,4,5-(OCH$_3$)$_3$—$C_6H_2$ |
| A.89 | H | 2-CH$_3$, 4-OCH$_3$—$C_6H_3$ |
| A.90 | H | 2-Cl, 4-OCH$_3$—$C_6H_3$ |
| A.91 | H | 4-OCF$_3$—$C_6H_4$ |
| A.92 | H | 2-OCHF$_2$—$C_6H_4$ |
| A.93 | H | 3-OCHF$_2$—$C_6H_4$ |
| A.94 | H | 4-OCHF$_2$—$C_6H_4$ |
| A.95 | H | 4-(OCF$_2$CHF$_2$)—$C_6H_4$ |
| A.96 | H | 2-F, 4-OCHF$_2$—$C_6H_3$ |
| A.97 | H | 4-(OCH$_2$CH$_3$)—$C_6H_4$ |
| A.98 | H | 4-[OC(CH$_3$)$_3$]—$C_6H_4$ |
| A.99 | H | 3-(CO$_2$CH$_3$)—$C_6H_4$ |
| A.100 | H | 4-(CO$_2$CH$_3$)—$C_6H_4$ |
| A.101 | H | 4-[CO$_2$C(CH$_3$)$_3$]—$C_6H_4$ |
| A.102 | H | 2,3-[O—CH$_2$—O]—$C_6H_3$ |
| A.103 | H | 3,4-[O—CH$_2$—O]—$C_6H_3$ |
| A.104 | H | 3,4-[O—C(CH$_3$)$_2$—O]—$C_6H_3$ |
| A.105 | H | 3,4-[O—CH$_2$CH$_2$—O]—$C_6H_3$ |
| A.106 | H | 2,3-[(CH$_2$)$_4$]—$C_6H_3$ |
| A.107 | H | 3,4-[(CH$_2$)$_4$]—$C_6H_3$ |
| A.108 | H | 4-[C(=NOCH$_3$)CH$_3$]—$C_6H_4$ |
| A.109 | H | 4-[C(=NOC$_2$H$_5$)CH$_3$]—$C_6H_4$ |
| A.110 | H | 4-[C(=NOCH$_3$)C$_2$H$_5$]—$C_6H_4$ |
| A.111 | H | 2-Cl, 4-[C(=NOCH$_3$)CH$_3$]—$C_6H_3$ |
| A.112 | H | 2-Me,4-[C(=NOCH$_3$)CH$_3$]—$C_6H_3$ |
| A.113 | H | 3-[C(=NOCH$_3$)CH$_3$]$C_6H_4$ |
| A.114 | H | 3-[C(=NOC$_2$H$_5$)CH$_3$]—$C_6H_4$ |
| A.115 | H | 3-[C(=NOCH$_3$)C$_2$H$_5$]—$C_6H_4$ |
| A.116 | H | 2-Cl, 3-[C(=NOCH$_3$)CH$_3$]—$C_6H_3$ |
| A.117 | H | 2-CH$_3$, 5-[C(=NOCH$_3$)CH$_3$]$C_6H_3$ |
| A.118 | H | 3,4-[OCF$_2$CF$_2$O]—$C_6H_3$ |
| A.119 | H | 3,4-[OCCl$_2$O]—$C_6H_3$ |
| A.120 | H | 2,3-[OCF$_2$O]—$C_6H_3$ |
| A.121 | H | 3,4-[OCF$_2$O]—$C_6H_3$ |
| A.122 | H | CH$_2$—$C_6H_5$ |
| A.123 | H | CH$_2$-[4-Cl—$C_6H_4$] |
| A.124 | H | CH$_2$-[1,4-Cl—$C_6H_3$] |
| A.125 | H | CH$_2$-[4-OCH$_3$—$C_6H_4$] |
| A.126 | H | CH$_2$-[2,4-(OCH$_3$)$_2$—$C_6H_3$] |
| A.127 | H | CH$_2$-[4-CN—$C_6H_4$] |
| A.128 | H | CH$_2$-[3-CF$_3$—$C_6H_4$] |
| A.129 | H | CH$_2$-[4-F, 2-Cl—$C_6H_3$] |
| A.130 | H | CH$_2$-[2-CN—$C_6H_4$] |
| A.131 | H | CH(CH$_3$)-[4-Cl—$C_6H_4$] |
| A.132 | H | CH(CH$_3$)-[2-CN—$C_6H_4$] |

TABLE A-continued

| No. | $R_n^1$ | $R^2$ |
|---|---|---|
| A.133 | H | CH(CH$_3$)-[3-OCHF$_2$—C$_6$H$_4$] |
| A.134 | H | C(=O)-[4-F—C$_6$H$_4$] |
| A.135 | H | C(=O)-[2,4-Cl$_2$—C$_6$H$_3$] |
| A.136 | H | C(=O)-[4-Me—C$_6$H$_4$] |
| A.137 | H | C(=O)-[3-CF$_3$—C$_6$H$_4$] |
| A.138 | H | C(=NOCH$_3$)-[4-Cl—C$_6$H$_4$] |
| A.139 | H | C(=NOCH$_3$)-[3-CF$_3$—C$_6$H$_4$] |
| A.140 | H | C(=NOCH$_3$)-[2,4-F$_2$—C$_6$H$_3$] |
| A.141 | H | C(=NOCH$_2$C≡CH)-[4-F—C$_6$H$_4$] |
| A.142 | H | CH$_2$-[5-Cl-2-pyridyl] |
| A.143 | H | CH$_2$-[6-Cl-3-pyridyl] |
| A.144 | H | CH$_2$-[3-isopropyl-5-isoxazolyl] |
| A.145 | H | CH$_2$-[1-phenyl-4-pyrazolyl] |
| A.146 | H | pyridin-2-yl |
| A.147 | H | 5-Cl-pyridin-2-yl |
| A.148 | H | 3,5-Cl$_2$-pyridin-2-yl |
| A.149 | H | 5-CF$_3$-pyridin-2-yl |
| A.150 | H | 3-Cl, 5-CF$_3$-pyridin-2-yl |
| A.151 | H | 3-Cl-pyridin-2-yl |
| A.152 | H | pyrazin-2-yl |
| A.153 | H | 5-Cl-pyrazin-2-yl |
| A.154 | H | pyridazin-2-yl |
| A.155 | H | 6-Cl-pyridazin-2-yl |

TABLE 13

Compounds of the formula where the radicals $R_n^1$ and $R^2$ have the meanings which correspond in each case to one line of Table B.

TABLE 14

Compounds of the formula where the radicals $R_n^1$ and $R^2$ have the meanings which correspond in each case to one line of Table B.

TABLE 15

Compounds of the formula where the radicals $R_n^1$ and $R^2$ have the meanings which correspond in each case to one line of Table B.

TABLE 16

Compounds of the formula where the radicals $R_n^1$ and $R^2$ have the meanings which correspond in each case to one line of Table B.

TABLE 17

Compounds of the formula where the radicals $R_n^1$ and $R^2$ have the meanings which correspond in each case to one line of Table B.

TABLE 18

Compounds of the formula

TABLE 19

Compounds of the formula

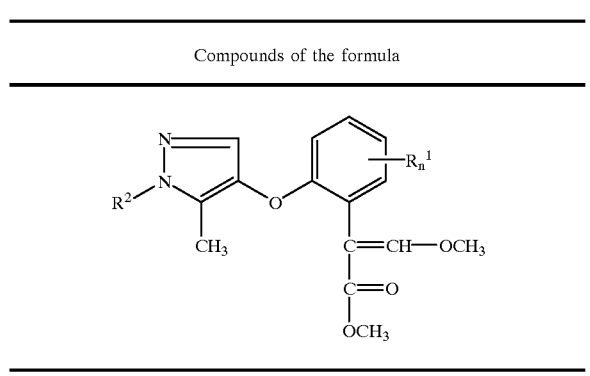

where the radicals $R_n^1$ and $R^2$ have the meanings which correspond in each case to one line of Table B.

TABLE 20

Compounds of the formula

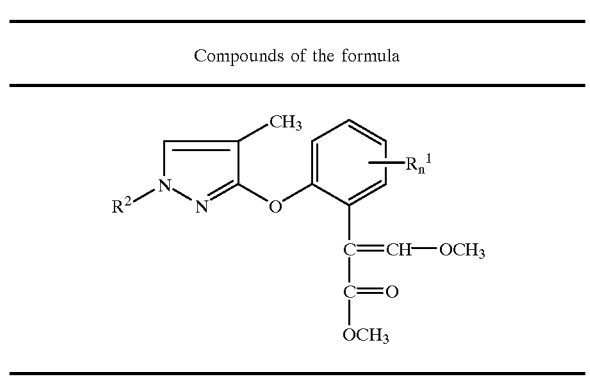

where the radicals $R_n^1$ and $R^2$ have the meanings which correspond in each case to one line of Table B.

TABLE 21

Compounds of the formula

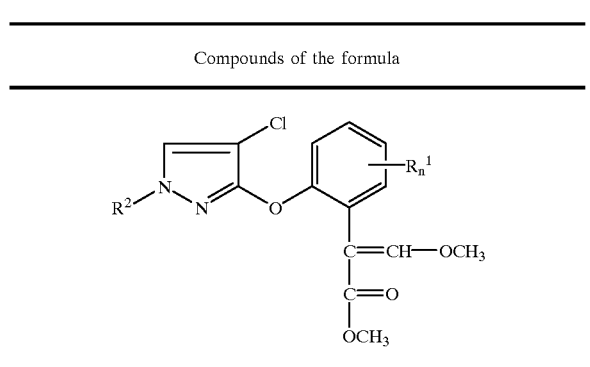

where the radicals $R_n^1$ and $R^2$ have the meanings which correspond in each case to one line of Table B.

TABLE 22

Compounds of the formula

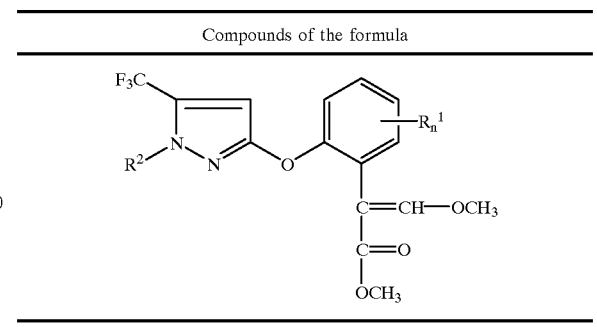

where the radicals $R_n^1$ and $R^2$ have the meanings which correspond in each case to one line of Table B.

TABLE 23

Compounds of the formula

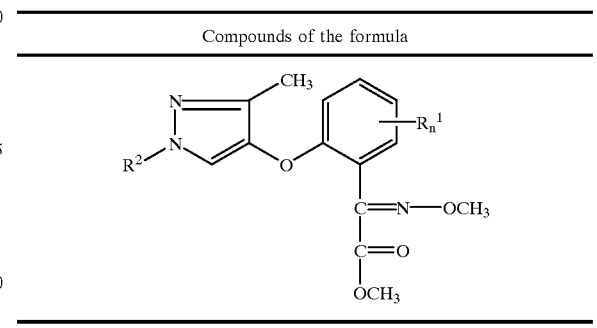

where the radicals $R_n^1$ and $R^2$ have the meanings which correspond in each case to one line of Table B.

TABLE 24

Compounds of the formula

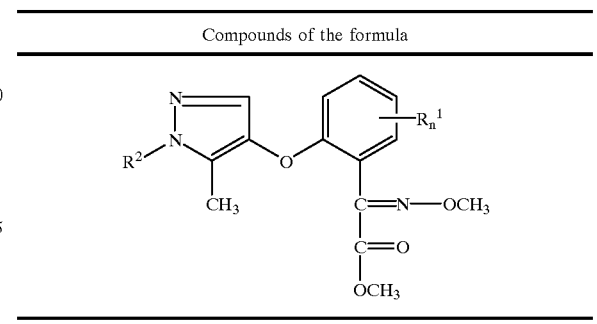

where the radicals $R_n^1$ and $R^2$ have the meanings which correspond in each case to one line of Table B.

TABLE 25

Compounds of the formula

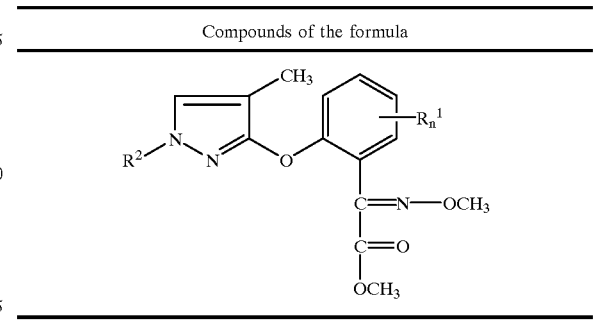

TABLE 26

Compounds of the formula

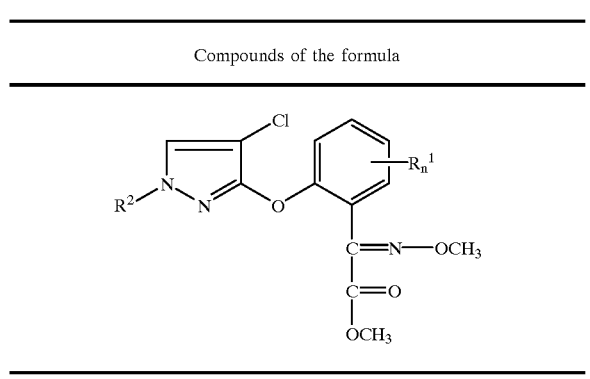

where the radicals $R_n^1$ and $R^2$ have the meanings which correspond is in each case to one line of Table B.

TABLE 27

Compounds of the formula

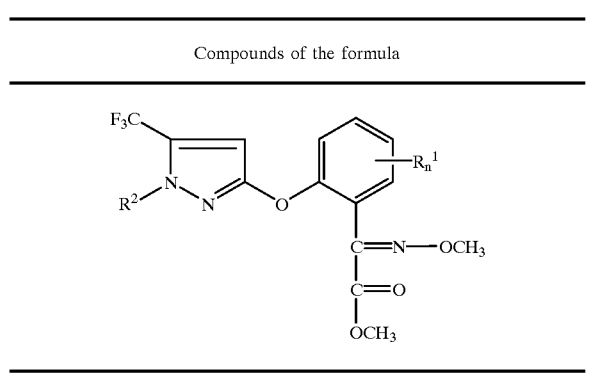

where the radicals $R_n^1$ and $R^2$ have the meanings which correspond in each case to one line of Table B.

TABLE 28

Compounds of the formula

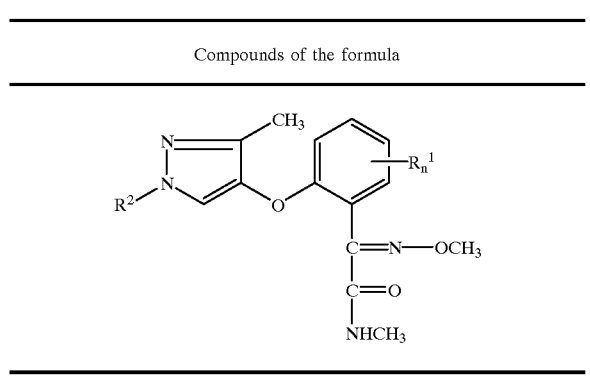

where the radicals $R_n^1$ and $R^2$ have the meanings which correspond in each case to one line of Table B.

TABLE 29

Compounds of the formula

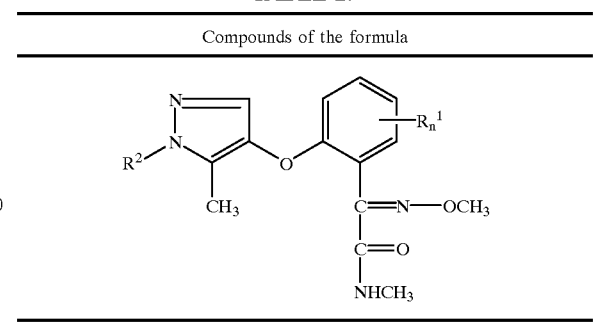

where the radicals $R_n^1$ and $R^2$ have the meanings which correspond in each case to one line of Table B.

TABLE 30

Compounds of the formula

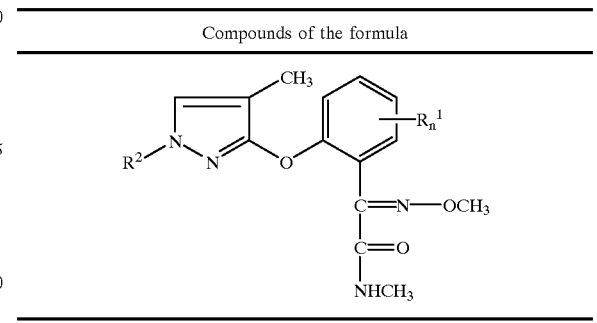

where the radicals $R_n^1$ and $R^2$ have the meanings which correspond in each case to one line of Table B.

TABLE 31

Compounds of the formula

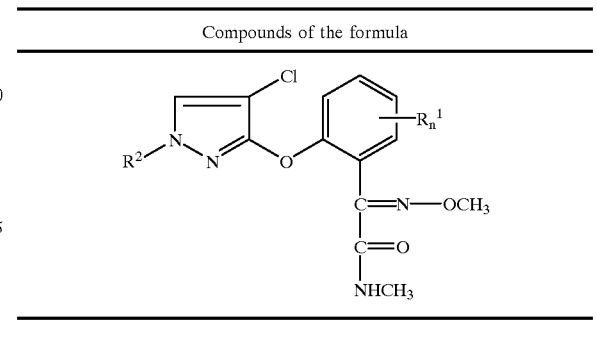

where the radicals $R_n^1$ and $R^2$ have the meanings which correspond in each case to one line of Table B.

TABLE 32

Compounds of the formula

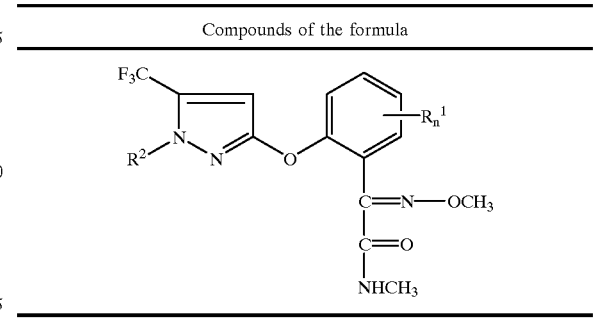

where the radicals $R_n^1$ and $R^2$ have the meanings which correspond in each case to one line of Table B.

TABLE B

| No. | $R_n^1$ | $R^2$ |
|---|---|---|
| B.1 | H | $C_6H_5$ |
| B.2 | H | 2-Cl—$C_6H_4$ |
| B.3 | H | 3-Cl—$C_6H_4$ |
| B.4 | H | 4-Cl—$C_6H_4$ |
| B.5 | 3-Cl | 4-Cl—$C_6H_4$ |
| B.6 | 4-OCH$_3$ | 4-Cl—$C_6H_4$ |
| B.7 | 6-Me | 4-Cl—$C_6H_4$ |
| B.8 | H | 2,4-Cl$_2$—$C_6H_3$ |
| B.9 | H | 4-F—$C_6H_4$ |
| B.10 | H | 2,4-F$_2$—$C_6H_3$ |
| B.11 | H | 2-Cl, 4-F—$C_6H_3$ |
| B.12 | H | 4-CF$_3$—$C_6H_4$ |
| B.13 | H | 3-CF$_3$—$C_6H_4$ |
| B.14 | H | 4-MeO—$C_6H_4$ |
| B.15 | H | 4-Me—$C_6H_4$ |
| B.16 | H | 2,4-Me$_2$—$C_6H_3$ |
| B.17 | H | 4-CN—$C_6H_4$ |
| B.18 | H | 2-CN—$C_6H_4$ |
| B.19 | H | 2-Cl, 4-CN—$C_6H_3$ |
| B.20 | H | 4-C(=NOCH$_3$)CH$_3$ |
| B.21 | H | 3-C(=NOCH$_3$)CH$_3$ |
| B.22 | H | 4-OCF$_3$ |
| B.23 | H | 4-OCHF$_2$ |
| B.24 | H | 3,4-[OCF$_2$O] |
| B.25 | H | CH$_2$-[4-Cl—$C_6H_4$] |
| B.26 | H | CH$_2$-[3-CF$_3$—$C_6H_4$] |
| B.27 | H | CH$_2$-[2-CN—$C_6H_4$] |
| B.28 | H | CH(CH$_3$)-[4-F—$C_6H_4$] |
| B.29 | H | C(=O)-[2,4-Cl$_2$—$C_6H_3$] |
| B.30 | H | C(=NOCH$_3$)-[4-Cl—$C_6H_4$] |
| B.31 | H | C(=NOCH$_3$)-[3-CF$_3$—$C_6H_4$] |
| B.32 | H | C(=NOCH$_3$)-[2,4-F$_2$—$C_6H_3$] |
| B.33 | H | CH$_2$-[5-Cl-2-pyridyl] |
| B.34 | H | CH$_2$-[6-Cl-3-pyridyl] |
| B.35 | H | 5-CF$_3$, 2-pyridyl |
| B.36 | H | 5-Cl, 2-pyridyl |
| B.37 | H | 6-Cl, 2-pyridyl |

The compounds I are suitable for controlling harmful fungi and animal pests.

Depending on their chemical and physical properties, they can be formulated with customary formulation auxiliaries, ie. those known to a skilled worker. The products of this process are termed "compositions".

Examples of suitable formulation auxiliaries are solid or liquid carriers, surfactants and tackifiers.

Liquid carriers are to be understood as meaning liquid solvents such as water and organic solvents, the latter acting as an auxiliary solvent, above all when the solvent used is water. The following can be used as organic solvents: aromatics such as xylene, toluene and alkylnaphthalenes, chlorinated aromatics or chlorinated aliphatic hydrocarbons such as chlorobenzenes, chloroethylenes and methylene chloride, aliphatic hydrocarbons such as cyclohexane and paraffins, eg. mineral oil fractions, alcohols such as butanol, iso-butanol, cyclohexanol and glycol, and the corresponding ethers and esters, ketones such as acetone, methyl ethyl ketone, methyl iso-butyl ketone and cyclohexanone, aprotic-dipolar solvents such as dimethylformamide, N-methyl-2-pyrrolidone and dimethyl sulfoxide.

Examples of suitable carriers are: ground natural minerals and mineral earths such as silicas, silicates, kaolins, clays, bole, loess, talc, chalk, limestone, lime, dolomite, magnesium oxide, quartz, attapulgite, montmorillonite and diatomaceous earth; ground synthetic minerals such as highly-disperse silica or meals of synthetic alumina and of synthetic silicates. Examples of solid carriers which are especially suitable for granules are: crushed and fractionated natural rocks such as calcite, marble, pumice, sepiolite; synthetic granules of inorganic and organic meals; granules of organic material such as sawdust, coconut shells, maize cobs or tobacco stalks.

Suitable surfactants are non-ionic and anionic emulsifiers/foam formers and dispersants:

fatty acid polyoxyethylene esters such as lauryl alcohol polyoxyethylene ether acetate, alkyl polyoxyethylene ethers or alkyl polyoxypropylene ethers, such as of iso-tridecyl alcohol, and fatty alcohol polyoxyethylene ethers, alkylaryl alcohol polyoxyethylene ethers such as octylphenyl polyoxyethylene ether, tributylphenyl polyoxyethylene ether, ethoxylated isooctylphenol, octylphenol or nonylphenol or castor oil, sorbitol esters, arylsulfonic acids, alkylsulfonic acids, alkylsulfuric acids, alkali metal salts, alkaline earth metal salts and ammonium salts of arylsulfonic acids,.eg. ligno-, phenol-, naphthalene and dibutylnaphthalenesulfonic acid, of alkylsulfonic acids, of alkylarylsulfonic acids, of alkylsulfuric acids, of lauryl ether sulfuric acids and of fatty alcohol sulfuric acids, of fatty acids, of sulfated hexa-, hepta- and octadecanols and of fatty alcohol glycol ethers, condensates of sulfonated naphthalene and its derivatives with formaldehyde, condensates of naphthalene sulfonic acids with phenol and formaldehyde, protein hydrolysates and in particular as dispersants: lignin-sulfite waste liquors and methylcellulose.

Examples of suitable tackifiers are: carboxymethylcellulose; natural and synthetic polymers in the form of powders, granules or latices such as gum arabic, polyvinyl alcohol, polyvinyl acetate, natural phospholipids such as cephalins and lecithins, synthetic phospholipids.

The compositions can furthermore comprise one or more representatives of the following groups of substances: colorants, other known active ingredients, trace nutrients and further additives.

Suitable colorants are, for example, inorganic pigments such as iron oxide, titanium oxide, Prussian Blue, and furthermore organic pigments such as alizarin, azo and metal phthalocyanin dyestuffs. Other known active ingredients are to be understood as meaning, for example, other fungicides, or else insecticides, acaricides, herbicides and growth regulators. Trace nutrients are, for example, salts of iron, manganese, boron, copper, cobalt, molybdenum and zinc. Examples of other additives which are suitable are mineral and vegetable oils.

In addition, the compositions can be mixed with other components which are important under practice conditions, such as fertilizers or other finished compositions comprising active ingredient.

The compositions are prepared in a manner known per se, ie. depending on the chemical and physical properties of the substances employed, for example by mixing, concomitant grinding, spraying on, extruding, granulating or dissolving in water, the latter, if appropriate, with the aid of an organic solvent. Powders, materials for spreading and dust can be obtained, for example, by mixing or concomitantly grinding the compounds I with a solid carrier.

Depending on the substances employed, the compositions are, for example, solutions, emulsions, suspensions, powders, foams, pastes, granules, aerosols or microencapsulations in polymeric substances or in coating compositions for seed.

For use, the compositions, which are normally commercially available in the form of concentrates, are, if required, dissolved, diluted and the like in the customary manner, normally using water in the case of wettable powders, water-dispersible granules, emulsifiable concentrates, dispersions and in some cases also microgranules. Preparations in the form of dusts, granulated preparations and sprayable solutions are in most cases not diluted further with other inert substances prior to use.

The compositions are applied in a manner known per se, for example by spraying, atomizing, dusting, spreading or pouring. As a rule, the plants are sprayed or dusted with the compositions. Alternatively or additionally, the seeds of the plants are treated in a manner known per se.

Examples of such preparations are:

I. a solution of 90 parts by weight of a compound I according to the invention and 10 parts by weight of N-methyl-2-pyrrolidone; this solution is suitable for use in the form of microdrops;

II. a mixture of 20 parts by weight of a compound I according to the invention, 80 parts by weight of xylene, 10 parts by weight of the adduct of 8 to 10 mol of ethylene oxide to 1 mol of oleic acid N-monoethanolamide, 5 parts by weight of calcium dodecylbenzenesulfonate, 5 parts by weight of adduct of 40 mol of ethylene oxide to 1 mol of castor oil: a dispersion is obtained by finely distributing the solution in water;

III. an aqueous dispersion of 20 parts by weight of a compound I according to the invention, 40 parts by weight of cyclohexanone, 30 parts by weight of isobutanol, 20 parts by weight of the adduct of 40 mol of ethylene oxide and 1 mol of castor oil;

IV. an aqueous dispersion of 20 parts by weight of a compound I according to the invention, 25 parts by weight of cyclohexanol, 65 parts by weight of a mineral oil fraction of boiling point 210 to 280° C. and 10 parts by weight of the adduct of 40 mol of ethylene oxide and 1 mol of castor oil;

V. a mixture, ground in a hammer mill, of 80 parts by weight of a compound I according to the invention, 3 parts by weight of sodium diisobutylnaphthalene-1-sulfonate, 10 parts by weight of the sodium salt of a lignosulfonic acid from a sulfite waste liquor and 7 parts by weight of pulverulent silica gel: a spray mixture is obtained by finely distributing the mixture in water;

VI. an intimate mixture of 3 parts by weight of a compound I according to the invention and 97 parts by weight of finely divided kaolin; this dust comprises 3% by weight of active ingredient;

VII. an intimate mixture of 30 parts by weight of a compound I according to the invention, 92 parts by weight of pulverulent silica gel and 8 parts by weight of paraffin oil which had been sprayed onto the surface of this silica gel; this formulation imparts good adhesion to the active ingredient;

VIII. a stable aqueous dispersion of 40 parts by weight of a compound I according to the invention, 10 parts by weight of the sodium salt of a phenolsulfonic acid/urea/ formaldehyde condensate, 2 parts by weight of silica gel and 48 parts by weight of water; this dispersion can be diluted further;

IX. a stable oily dispersion of 20 parts by weight of a compound I according to the invention, 2 parts by weight of calcium dodecylbenzenesulfonate, 8 parts by weight of fatty alcohol polyglycol ether, 20 parts by weight of the sodium salt of phenolsulfonic acid/urea/formaldehyde condensate and 68 parts by weight of a paraffinic mineral oil.

If the compounds I are applied as such, the most important factor is that they are evenly distributed.

The compounds I, their salts and the compositions according to the invention are distinguished by an outstanding activity against a broad spectrum of harmful fungi (phytopathogenic fungi), in particular from the classes of the Ascomycetes,
Basidiomycetes,
Deuteromycetes and
Phycomycetes.

Some of them act systemically and can be employed as foliar- and soil-acting fungicides.

They are especially important for controlling a large number of fungi on a variety of crop plants such as wheat, rye, barley, oats, rice, maize, grass, cotton, soybeans, coffee, sugar cane, grapevines, fruit species, ornamentals and vegetables such as cucumbers, beans and cucurbits, and on the seeds of these plants.

The compounds I, their salts and the compositions according to the invention are applied by treating the harmful fungi, their environment, or the seeds, plants, areas, materials or spaces to be protected against fungal infection, with a fungicidally effective amount of the compositions or of the compounds I or their salts. Application can be effected before or after infection by the fungi.

Specifically, the compounds I and the compositions according to the invention are suitable for controlling the following plant diseases:

Erysiphe graminis (powdery mildew) in cereals, Erysiphe cichoracearum and Sphaerotheca fuliginea on cucurbits, Podosphaera leucotricha on apples, Uncinula necator on grapevines, Puccinia species on cereals, Rhizoctonia species on cotton, rice and lawns, Ustilago species on cereals and sugar cane, Venturia inaequalis (scab) on apples, Helminthosporium species on cereals, Septoria nodorum on wheat, Botrytis cinerea (gray mold) on strawberries, grapevines, ornamentals and vegetables, Cercospora arachidicola on peanuts, Pseudocercosporella herpotrichoides on wheat, barley, Pyricularia oryzae on rice, Phytophthora infestans on potatoes and tomatoes, Fusarium and Verticillium species on a variety of plants, Plasmopara viticola on grapevines, Pseudoperonospora species in hops and cucumbers, Alternaria species on vegetables and fruit.

In general, the fungicidal compositions comprise from 0.1 to 95, preferably from 0.5 to 90% by weight of active ingredient.

Depending on the nature of the desired effect, the application rates are from 0.01 to 2.0 kg of active ingredient per ha.

In the treatment of seeds, amounts of from 0.001 to 0.1 g, preferably from 0.01 to 0.05 g, of active ingredient are generally required per kilogram of seed.

In their use form as fungicides, the compositions according to the invention can also be present together with other active ingredients, eg. with herbicides, insecticides, growth regulators, fungicides or else with fertilizers.

A mixture with fungicides frequently results in a widened fungicidal spectrum of action.

The following list of fungicides together with which the compounds according to the invention can be used is intended to illustrate the possible combinations, but not to impose any limitation:

sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide;

nitro derivatives, such as dinitro(1-methylheptyl)phenyl crotonate, 2-sec-butyl-4,6-dinitrophenyl-3,3-dimethyl acrylate, 2-sec-butyl-4,6-dinitrophenyl isopropyl carbonate, di-isopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis (dimethylamino)phosphinyl]-3-phenyl-1,2,4-triazole, 2,3-dicyano-1,4-dithioanthraquinone, 2-thio-1,3-dithiolo [4,5-b]quinoxaline, methyl 1-(butylcarbamoyl)-2-benzimidazolecarbamate, 2-methoxcarbonylaminobenzimidazole, 2-(2-furyl) benzimidazole, 2-(4-thiazolyl)benzimidazole, N-(1,1,2,2-tetrachloroethylthio)-tetrahydrophthalimide, N-trichloromethylthiotetrahydrophthalimide, N-trichloromethylthiophthalimide, N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diyl-bis(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]- piperidine, 1-[2-(2,4-dichlorophenyl)-4-ethyl-1,3-dioxolan-2-ylethyl]-1H-1,2,4-triazole, 1-[2-(2, 4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1, 2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)-benzene, and a variety of fungicides, such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)- alanine methyl ester, N-(2,6-dimethylphenyl)-N-chloroacetyl-D, L-2-aminobutyrolactone, DL-N-(2,6-dimethylphenyl)-N-(phenyl-acetyl)alanine methyl ester, 5-methyl-5-vinyl-3-(3,5-dichlorophenyl)-2,4-dioxo-1,3-oxazolidine, 3-[3,5-dichlorophenyl-(5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]-acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methyl-silyl)methyl)-1H-1,2,4-triazole, strobilurins such as methyl-E-methoximino-[α-(o-tolyloxy)-o-tolyl]acetate, methyl E-2-{2-[6-(2-cyanophenoxy) pyrimidin-4-yloxy]phenyl}-3-methoxyacrylate, N-methyl-E-methoximino-[α-(2-phenoxyphenyl)] acetamide, N-methyl-E-methoximino-[α-(2,5-dimethylphenoxy)-o-tolyl]acetamide, anilinopyrimidines such as N-(4,6-dimethylpyrimidin-2-yl) aniline, N-(4-methyl-6-(1-propynyl)pyrimidin-2-yl] aniline, N-(4-methyl-6-cyclopropylpyrimidin-2-yl) aniline, phenylpyrroles such as 4-(2,2-difluoro-1,3-benzodioxol-4-yl)-pyrrole-3-carbonitrile, cinnamamides such as 3-(4-chlorophenyl)-3-(3,4-dimethoxyphenyl) acryloylmorpholine, (2RS,3SR)-1-[3-(2-chlorophenyl)-2-[4-fluorophenyl] oxiran-2-yl-methyl]-1H-1,2,4-triazole.

Moreover, the compounds of the formula I are suitable for effectively controlling animal pests, above all from the classes of the insects, arachnids and nematodes. They can be employed as pesticides in crop protection and in the hygiene, stored-product and veterinary sector.

The harmful insects include, from the order of the lepidopterans (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Putella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus* vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus, Sitophilus granaria.

From the order of the dipterans (Diptera), for example, Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.

From the order of the thrips (Thysanoptera), for example, Frankliniella fusca, Frankliniella occidentalis, Frankliniella tritici, Scirtothrips citri, Thrips oryzae, Thrips palmi, Thrips tabaci.

From the order of the hymenopterans (Hymenoptera), for example, Athalia rosae, Atta cephalotes, Atta sexdens, Atta texana, Hoplocampa minuta, Hoplocampa testudinea, Monomorium pharaonis, Solenopsis geminata, Solenopsis invicta.

From the order of the heteropterans (Heteroptera), for example, Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.

From the order of the homopterans (Homoptera), for example, Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.

From the order of the termites (Isoptera), for example, Calotermes flavicollis, Leucotermes flavipes, Reticulitermes lucifugus, Termes natalensis.

From the order of the orthopterans (Orthoptera), for example, Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.

From the class of the Arachnoidea, for example, arachnids (Acarina) such as Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.

From the class of the nematodes, for example, root-knot nematodes, eg. Meloidogyne hapla, Meloidogyne incognita, Meloidogyne javanica, cyst-forming nematodes, eg. Globodera rostochiensis, Heterodera avenae, Heterodera glycines, Heterodera schachtii, Heterodera trifolii, stem eel worms and foliar nematodes, eg. Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.

The concentrations of active ingredient in the ready-to-use preparations can be varied within substantial ranges. In general, they are from 0.0001 to 10%, preferably from 0.01 to 1%.

The active ingredients can also be used successfully in the ultra-low volume method (ULV), it being possible to apply formulations with over 95% by weight of active ingredient, or even the active ingredient without additives.

Under the conditions in the open, the application rate of active ingredient for controlling pests is from 0.1 to 2.0, preferably from 0.2 to 1.0 kg/ha.

Synthesis examples

The protocols given in the synthesis examples which follow can be used for obtaining other representatives of the compounds I and IV by modifying the starting compounds. The physical data of the products prepared in accordance with these protocols are shown in the tables which follow.

The chemical shifts (in ppm) of the $^1$H NMR spectra were measured against tetramethylsilane (br=broad signal, s=singulet, d=doublet, m=multiplet).

EXAMPLE 1

Methyl 2-[1-(4-chlorophenyl)-3-pyrazolyloxy] phenylglyoxalate

A solution of 4.2 g of methyl 2-fluorophenylglyoxalate in 30 ml of anhydrous dimethyl sulfoxide was added dropwise to a solution of 5.0 g of the potassium salt of 1-(4-chlorophenyl)-3-hydroxy-pyrazole in 30 ml of anhydrous dimethyl sulfoxide. The batch was heated at 60° C. for 3.5 more hours, cooled and divided into two halves. One half was poured into ice-water/methyl tert-butyl ether for working-up. After the organic phase had been separated off, the aqueous phase was extracted three more times with methyl tert-butyl ether. The combined organic phases were dried over sodium sulfate and concentrated. The crude product was purified by chromatography over silica gel (eluent heptane/ethyl acetate 80/20→70/30). This gave 1.0 g of the title compound as a pale oil.

$^1$H NMR (CDCl$_3$): 3.85 (s,3H); 6.1 (d,1H); 7.25 (d,1H); 7.3–7.6 (m,6H); 7.8 (d,1H); 7.95 (d,1H).

TABLE C

IV (W = —CO—CO—Y—CH$_3$)

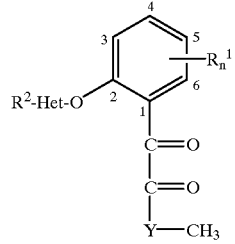

| No. | Y | R$^1_n$ | R$^2$-Het | Physical data (m.p. [° C.], IR [cm$^{-1}$]), $^1$H-NMR in CDCl$_3$ [ppm] |
|---|---|---|---|---|
| C.001 | O | H | 1-(4-chlorophenyl)pyrazol-3-yl | 1744, 1678, 1538, 1463, 1454, 1205 |
| C.002 | O | H | 1-(4-fluorophenyl)pyrazol-3-yl | 1745, 1683, 1537, 1466, 1206 |
| C.003 | O | H | 1-(2,4-dichlorophenyl)pyrazol-3-yl | 71–72 |
| C.004 | O | H | 1-(4-chlorophenyl)-5-methylpyrazol-4-yl | 2.2(3H); 3.9(3H); 6.95(1H); 7.15(1H); 7.3–7.6(5H); 7.95(1H) |
| C.005 | O | H | 1-(2,4-difluorophenyl)pyrazol-4-yl | 64–66 |
| C.006 | O | H | 1-(4-chlorophenyl)pyrazol-4-yl | 3.85(3H); 7.05(1H); 7.2(1H); 7.4(2H); 7.45–7.67(4H); 7.8(1H); 7.9(1H) |
| C.007 | O | H | 1-phenylpyrazol-4-yl | 3.85(3H); 7.1(1H); 7.15–7.3(2H); 7.4–7.7 (6H); 7.85(1H); 7.95(1H) |
| C.008 | O | H | 1-(4-cyanophenyl)pyrazol-4-yl | 109–111 |
| C.009 | O | H | 1-(4-methylphenyl)pyrazol-4-yl | 97–98 |
| C.010 | O | H | 1-(4-fluorophenyl)pyrazol-4-yl | 75–77 |
| C.011 | O | H | 1-(2-chloro,4-methylphenyl)pyrazol-4-yl | 2.4(3H); 3.85(3H); 7.1–7.3(3H); 7.35 (1H); 7.4–7.75(3H); 7.8(1H); 7.9(1H) |
| C.012 | O | H | 1-(2,4-dimethoxybenzyl)pyrazol-3-yl | 3.8(3H); 3.85(3H); 3.0(3H); 5.2(2H); 5.8(1H); 6.5(2H); 7.1–7.3(4H); 7.5(1H); 7.9(1H) |
| C.013 | O | H | 1-(2,4-dichlorobenzyl)pyrazol-3-yl | 1745, 1600, 1472, 1264, 1204 |

EXAMPLE 2

Methyl E-2-methoxyimino-2-(2-[1-(4-chlorophenyl)-3-pyrazolyloxy]-phenyl)acetate

Approximately 30 ml of methanol and 2.88 g of O-methylhydroxyl-amino hydrochloride were added to the second half of the dimethyl sulfoxide solution of Example 1. The mixture was stirred for a further 12 hours at room temperature, and the batch was worked up as described for Example 1. The dried methyl tert-butyl ether phase was filtered through silica gel. After evaporation of the residue on a rotary evaporator, there remained 3.2 g of crude product. To concentrate the desired E isomer, the crude product was taken up in 50 ml of saturated methanolic hydrochloric acid, and the mixture was stirred for 3 hours at room temperature. For working-up, the mixture was treated with methyl tert-butyl ether. The organic phase was washed with sodium chloride solution until neutral, dried over sodium sulfate and concentrated. Some of the remaining oil crystallized. After trituration with diisopropyl ether, 1.05 g of the title compound were obtained as colorless solid.

M.p. [°C]: 109–110° C. $^1$H NMR (CDCl$_3$): 3.8 (s,3H); 4.05 (s,3H); 5.95 (d,1H); 7.1–7.7 (m,8H); 7.8 (d,1H).

EXAMPLE 3

N-methyl-E-2-methoxyimino-2-(2-[1-(4-chlorophenyl)-3-pyrazolyl-oxymethyl]phenylacetamide 0.6 g of the methyl ester of Example 2 were dissolved in 40 ml of tetrahydrofuran, and 1 ml of 40% strength aqueous methylamine solution was added. The mixture was stirred overnight at room temperature, the batch was concentrated, and the residue was taken up in 50 ml of methyl tert-butyl ether. The organic phase was extracted with water, and the extract was dried over sodium sulfate and subsequently evaporated to dryness. There remained 0.3 g of the title compound as colorless solid.

M.p. [°C]: 186–187° C. $^1$H NMR (CDCl$_3$): 2.85 (d,3H); 3.9 (s,3H); 6.0 (d,1H); 6.8 (br,NH); 7.2–7.6 (m,8H); 7.8 (d,1H).

EXAMPLE 4

Methyl E-α-{2-(1-[4-chlorophenyl]-3-pyrazolyloxy) phenyl}-β-methoxyacrylate

A solution of 0.38 g of potassium tert-butoxide in 3 ml of tetrahydrofuran was added dropwise at not more than 5° C to a suspension of 1.4 g of methoxymethyltriphenylphosphonium bromide ("Wittig reagent") in 15 ml of anhydrous tetrahydrofuran. 1.0 g of methyl 2-[1-(4-chlorophenyl)-3-pyrazolyloxy]phenylglyoxalate (cf. Ex. 1) in 5 ml of tetrahydrofuran was added to the dark red suspension, and the batch was allowed to come to room temperature. Wittig reagent was metered in twice more until all of the keto ester had reacted. For working-up, the batch was stirred into 20% by weight of aqueous citric acid and the mixture was extracted three times with methyl tert-butyl ether. The combined organic phases were washed until neutral, dried over sodium sulfate and subsequently concentrated. The crude product (3.2 g) was chromatographed over silica gel (eluent: toluene/ethyl acetate, 95/5). The resulting E/Z mixture was separated by medium-pressure chromatography on silica gel (eluent heptane/ethyl acetate, 9/1→7/3). This gave 0.5 g of the title compound and 0.15 g of the Z isomer.

E compound: m.p. 109–110° C. ¹H NMR (CDCl₃): 3.65 (s,3H); 3.8 (s,3H); 5.95 (d,1H); 7.1–7.4 (m,6H); 7.5 (s,1H); 7.55 (d,2H); 7.75 (d,1H).

Z compound: ¹H NMR (CDCl₃): 3.6 (s,3H); 3.85 (s,3H); 5.9 (d,1H);

6.7 (s,1H); 7.1–7.3 (m,4H); 7.35 (d,2H); 7.55 (d,2H); 7.75 (d,1H).

TABLE D

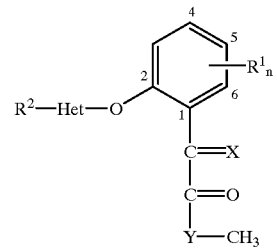

I

| No. | X | Y | $R^1_n$ | $R^2$-Het | Physical data (m.p. [° C.], IR [cm⁻¹]), ¹H NMR in CDCl₃ [ppm] |
|---|---|---|---|---|---|
| D.001 | E-NOCH₃ | O | H | 1-(4-chlorophenyl)pyrazol-3-yl | 109–110 |
| D.002 | E-NOCH₃ | NH | H | 1-(4-chlorophenyl)pyrazol-3-yl | 186–187 |
| D.003 | E-CHOCH₃ | O | H | 1-(4-chlorophenyl)pyrazol-3-yl | 109–110 |
| D.004 | Z-CHOCH₃ | O | H | 1-(4-chlorophenyl)pyrazol-3-yl | cf. ¹H NMR data in Example 4 |
| D.005 | E-NOCH₃ | O | H | 1-(4-fluorophenyl)pyrazol-3-yl | 89–90 |
| D.006 | E-NOCH₃ | NH | H | 1-(4-fluorophenyl)pyrazol-3-yl | 157–159 |
| D.007 | E-NOCH₃ | O | H | 1-(2,4-dichlorophenyl)pyrazol-3-yl | 138–139 |
| D.008 | E-NOCH₃ | NH | H | 1-(2,4-dichlorophenyl)pyrazol-3-yl | 108–111 |
| D.009 | E-NOCH₃ | O | H | 3-(2,4-dichlorophenyl)pyrazol-1-yl | 124–126 |
| D.010 | E-NOCH₃ | NH | H | 3-(2,4-dichlorophenyl)pyrazol-1-yl | 3.0(3H); 4.0(3H); 6.75(1H); 6.85(1H); 7.1–7.3(4H); 7.4 (1H); 7.55(1H); 7.8(1H) |
| D.011 | E-NOCH₃ | O | H | 1-(4-chlorophenyl),5-methyl-pyrazol-4-yl | 129–131 |
| D.012 | E-NOCH₃ | NH | H | 1-(4-chlorophenyl),5-methyl-pyrazol-4-yl | 148–151 |
| D.013 | E-CHOCH₃ | O | H | 1-(4-chlorophenyl),5-methyl-pyrazol-4-yl | 114–151 |
| D.014 | E-CHOCH₃ | O | H | 1-(2,4-difluorophenyl)pyrazol-4-yl | 97–99 |
| D.015 | E-NOCH₃ | O | H | 1-(2,4-difluorophenyl)pyrazol-4-yl | 103–104 |
| D.016 | E-NOCH₃ | NH | H | 1-(2,4-difluorophenyl)pyrazol-4-yl | 80–82 |
| D.017 | E-CHOCH₃ | O | H | 1-(4-chlorophenyl)pyrazol-4-yl | 86–88 |
| D.018 | E-NOCH₃ | O | H | 1-(4-chlorophenyl)pyrazol-4-yl | 103–105 |
| D.019 | E-NOCH₃ | NH | H | 1-(4-chlorophenyl)pyrazol-4-yl | 3410, 3095, 1699, 1498, 1377, 1027 |
| D.020 | E-CHOCH₃ | O | H | 1-phenylpyrazol-4-yl | 2950, 1708, 1502, 1254, 1129 |
| D.021 | E-NOCH₃ | O | H | 1-phenylpyrazol-4-yl | 68–70 |
| D.022 | E-NOCH₃ | NH | H | 1-phenylpyrazol-4-yl | 118–119 |
| D.023 | E-CHOCH₃ | O | H | 1-(4-cyanophenyl)pyrazol-4-yl | 3120, 2220, 1695, 1516, 1384, 1247 |
| D.024 | E-NOCH₃ | O | H | 1-(4-cyanophenyl)pyrazol-4-yl | 128–129 |
| D.025 | E-NOCH₃ | MH | H | 1-(4-cyanophenyl)pyrazol-4-yl | 178–180 |
| D.026 | E-CHOCH₃ | O | H | 1-(4-methylphenyl)pyrazol-4-yl | 123–125 |
| D.027 | E-NOCH₃ | O | H | 1-(4-methylphenyl)pyrazol-4-yl | 132–135 |
| D.028 | E-NOCH₃ | NH | H | 1-(4-methylphenyl)pyrazol-4-yl | 110–112 |
| D.029 | E-CHCH₃ | O | H | 1-(4-methylphenyl)pyrazol-4-yl | 1714, 1517, 1362, 1258, 816, |
| D.030 | E-CHOCH₃ | O | H | 1-(4-fluorophenyl)pyrazol-4-yl | 1708, 1514, 1253, 1230, 1129 |
| D.031 | E-NOCH₃ | O | H | 1-(4-fluorophenyl)pyrazol-4-yl | 76–78 |
| D.032 | E-NOCH₃ | NH | H | 1-(4-fluorophenyl)pyrazol-4-yl | 138–140 |
| D.033 | E-CHOCH₃ | O | H | 1-(2-chloro,4-methylphenyl)pyrazol-4-yl | 2935, 1710, 1509, 1253, 1129 |
| D.034 | E-NOCH₃ | O | H | 1-(2-chloro,4-methylphenyl)pyrazol-4-yl | 2940, 1729, 1509, 1072, 1011 |
| D.035 | E-NOCH₃ | NH | H | 1-(2-chloro,4-methylphenyl)pyrazol-4-yl | 119–120 |
| D.036 | E-CHOCH₃ | O | H | 1-(2,4-dichlorophenyl)pyrazol-4-yl | 1710, 1490, 1253, 1129, 1104 |
| D.037 | E-NOCH₃ | O | H | 1-(2,4-dichlorophenyl)pyrazol-4-yl | 84–86 |
| D.038 | E-NOCH₃ | O | H | 1-(2,4-dichlorophenyl)pyrazol-4-yl | 137–139 |
| D.039 | E-CHOCH₃ | O | H | 1-(2,4-dimethoxybenzyl)pyrazol-3-yl | 2940, 1709, 1509, 1476, 1209 |
| D.040 | E-CHOCH₃ | O | H | 1-(2,4-dichlorobenzyl)pyrazol-3-yl | 1709, 1474, 1254, 1129, 1104 |

Use examples

1. Example of the activity against harmful fungi

Fungicidal activity of the compounds of the formula I was demonstrated by the following experiments:

The active ingredients were formulated as a 20% emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Emulphor® EL (Emulan® EL, emulsifier based on ethoxylated fatty alcohols) and diluted with water to give the desired concentration. Evaluation was carried out visually.

2. Examples of the activity against animal pests

The activity of the compounds of the general formula I against animal pests was demonstrated by the following experiments:

The active ingredients were formulated a) as a 0.1% strength solution in acetone or b) as a 10% emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Emulphor® EL (Emulan® EL, emulsifier based on ethoxylated fatty alcohols)

and diluted to give the desired concentration, using acetone in the case of a) and water in the case of b).

After the experiments had been concluded, in each case the lowest concentration at which the compounds still caused an 80–100% inhibition or mortality in comparison with untreated controls was determined (limit or minimal concentration).

We claim:

1. A compound of the formula I

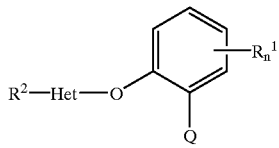

(I)

or a salt thereof where:

n is 0, 1, 2, 3 or 4, $R^1$ being the same or different when n is greater than 1;

Q is —C(=CHCH$_3$)—COOCH$_3$,
—C(=CHOCH3)—COOCH$_3$,
—C(=NOCH$_3$)—COOCH$_3$ or
—C(=NOCH$_3$)—CONH (CH$_3$);

Het is a pyrazole ring which has attached to it the radical $R^2$ and is further unsubstituted or substituted by one or two substituents selected from the group consisting of: chlorine, bromine, methyl and trifluoromethyl;

$R^1$ is nitro, cyano, halogen, $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio;

phenyl or phenoxy, each of which is unsubstituted or substituted by a member selected from the group consisting of halogen, one or, two or three of the following substitutents:

$C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio;

if n is greater than 1, a 1,3-butadiene-1,4-diyl group which is bonded to two adjacent carbon atoms of the phenyl radical and which is unsubstituted or substituted by halogen one or, two of the following substitutents:

nitro, cyano, $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio;

$R^2$ is hydrogen or an unsubstituted or substituted mono- or binuclear aromatic ring which is bonded directly or through a group (—CR$^3$R$^4$—) and which, besides carbon atoms, contains no hetero atom or contains one to four nitrogen atoms or one or two nitrogen atoms and one oxygen or sulfur atom or one oxygen or sulfur atom or one oxygen or sulfur atom as ring members, where $R^3$, $R^4$ independently of one another are: hydrogen or $C_1$-$C_4$-alkyl, or, together with the carbon atom to which they are bonded: a group (—C(=O)—) or (—C(=NOR$^5$)—), where, in turn, $R^5$ is $C_1$-$C_4$-alkyl or $C_2$-$C_4$-alkynyl.

2. A compound of the formula I or a salt thereof as claimed in claim 1 where the variables have the following meanings:

n is 0 or 1;

Het is a pyrazole ring which has attached to it the radical $R^2$ and which can additionally have attached to it one or two substituents selected from the group consisting of: chlorine, bromine, methyl and trifluoromethyl;

$R^1$ is halogen, $C_1$-$C_4$-alkyl, $C_1$-$C_2$-haloalkyl, $C_1$-$C_2$-alkoxy, $C_1$-$C_2$-haloalkoxy or $C_1$-$C_2$-alkylthio;

$R^2$ is an unsubstituted or substituted mono- or binuclear carbocyclic aromatic ring which is bonded directly.

3. A compound of the formula I or a salt thereof as claimed in claim 1 where Het has one of the following meanings, the free bond on the left side of the ring in each case having attached to it the radical $R^2$ as set forth in claim 1:

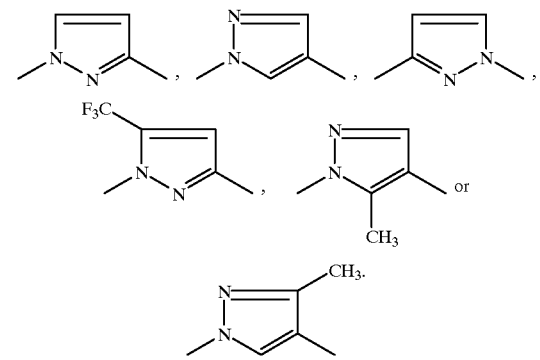

4. A composition which is suitable for controlling harmful fungi and animal pests, comprising an effective amount of a compound of the formula I or of a salt thereof as claimed in claim 1 and at least one formulation auxiliary.

5. A method of controlling harmful fungi and animal pests, which comprises treating the harmful fungi, their environment, or the plants, areas, materials or spaces to be kept free from them, with an effective amount of a compound of the formula I or of a salt thereof as claimed in claim 1.

* * * * *

UNITED STATES PATENT AND TRADEMARK OFFICE
CERTIFICATE OF CORRECTION

PATENT NO. : 6,075,149  
DATED : June 13, 2000  
INVENTOR(S) : Kirstgen et al.

Page 1 of 1

It is certified that error appears in the above-identified patent and that said Letters Patent is hereby corrected as shown below:

<u>Column 37, claim 1,</u>  
Line 47, "-C(=CHOCH3)-COOCH$_3$" should be -- -C(=CHOCH$_3$)-COOCH$_3$ --.

Signed and Sealed this

Fifth Day of February, 2002

Attest:

Attesting Officer

JAMES E. ROGAN  
*Director of the United States Patent and Trademark Office*